United States Patent
Kawano et al.

(10) Patent No.: US 8,529,433 B2
(45) Date of Patent: Sep. 10, 2013

(54) BODY-INSERTABLE APPARATUS SYSTEM

(75) Inventors: Hironao Kawano, Machida (JP); Shinsuke Tanaka, Hino (JP); Akio Uchiyama, Yokohama (JP)

(73) Assignee: Olympus Medical Systems Corp., Tokyo (JP)

(*) Notice: Subject to any disclaimer, the term of this patent is extended or adjusted under 35 U.S.C. 154(b) by 653 days.

(21) Appl. No.: 12/730,325

(22) Filed: Mar. 24, 2010

(65) Prior Publication Data

US 2010/0179381 A1 Jul. 15, 2010

Related U.S. Application Data

(63) Continuation of application No. PCT/JP2008/067331, filed on Sep. 25, 2008.

(30) Foreign Application Priority Data

Sep. 26, 2007 (JP) ................................. 2007-249970

(51) Int. Cl.
*A61B 1/00* (2006.01)

(52) U.S. Cl.
USPC ............ 600/101; 600/103; 600/104; 600/160

(58) Field of Classification Search
USPC ................... 600/101, 103, 104, 160; 396/17; 310/12.14
See application file for complete search history.

(56) References Cited

U.S. PATENT DOCUMENTS

| | | | |
|---|---|---|---|
| 8,032,320 B2* | 10/2011 | Sato et al. | 702/94 |
| 2003/0181788 A1* | 9/2003 | Yokoi et al. | 600/160 |
| 2004/0199054 A1 | 10/2004 | Wakefield | |
| 2005/0124875 A1 | 6/2005 | Kawano et al. | 600/407 |
| 2006/0030752 A1 | 2/2006 | Orihara | 600/109 |
| 2006/0167339 A1* | 7/2006 | Gilad et al. | 600/101 |
| 2006/0169293 A1 | 8/2006 | Yokoi et al. | 128/899 |

(Continued)

FOREIGN PATENT DOCUMENTS

| | | |
|---|---|---|
| JP | 6-114036 | 4/1994 |
| JP | 2002-000556 | 1/2002 |

(Continued)

OTHER PUBLICATIONS

International Search Report dated Nov. 11, 2008.

(Continued)

*Primary Examiner* — Clayton E Laballe
*Assistant Examiner* — Warren K Fenwick
(74) *Attorney, Agent, or Firm* — Scully, Scott, Murphy & Presser, P.C.

(57) ABSTRACT

A body-insertable apparatus system has a body insertable apparatus that is inserted into a subject and a control apparatus. The body-insertable apparatus includes a magnetic responding unit that is provided within a casing forming the body-insertable apparatus and has a magnetization direction; and a needle that is protruded and retracted with respect to a surface of the casing. The control apparatus includes a magnetic field generator that generates a magnetic field; and a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer.

19 Claims, 35 Drawing Sheets

(56) References Cited

U.S. PATENT DOCUMENTS

| | | | |
|---|---|---|---|
| 2007/0260105 A1* | 11/2007 | Uchiyama et al. | 600/12 |
| 2007/0265496 A1* | 11/2007 | Kawano et al. | 600/109 |
| 2008/0114204 A1* | 5/2008 | Fujimori et al. | 600/130 |
| 2008/0294143 A1 | 11/2008 | Tanaka et al. | 604/506 |
| 2008/0297291 A1* | 12/2008 | Kawano et al. | 335/285 |
| 2008/0306340 A1* | 12/2008 | Uchiyama et al. | 600/117 |
| 2009/0018396 A1* | 1/2009 | Takizawa et al. | 600/127 |
| 2009/0281387 A1 | 11/2009 | Takizawa et al. | 600/117 |
| 2010/0001592 A1* | 1/2010 | Kawano et al. | 310/12.14 |

FOREIGN PATENT DOCUMENTS

| | | |
|---|---|---|
| JP | 2003-275170 | 9/2003 |
| JP | 2003-325438 | 11/2003 |
| JP | 2004-222998 | 8/2004 |
| JP | 2004-275358 | 10/2004 |
| JP | 2005-124708 | 5/2005 |
| JP | 2006-43115 | 2/2006 |
| JP | 2007-151729 A | 6/2007 |
| WO | WO 2007/069697 A1 | 6/2007 |
| WO | WO 2007/074888 A1 | 7/2007 |
| WO | WO 2007/077895 A1 | 7/2007 |

OTHER PUBLICATIONS

European Search Report dated Nov. 7, 2012 from corresponding European Patent Application No. EP 08 83 3792.8.

European Office Action dated Jun. 19, 2013 from corresponding European Patent Application No. 08 833 792.8.

* cited by examiner (1)    (2)

(1)　　　　　　　　　　　　(2)

(1)    (2)

(1)    (2)

(1)  (2)

(1)  (2)

BODY-INSERTABLE APPARATUS SYSTEM

CROSS-REFERENCE TO RELATED APPLICATIONS

This application is a continuation of PCT international application Ser. No. PCT/JP2008/067331 filed on Sep. 25, 2008 which designates the United States, incorporated herein by reference, and which claims the benefit of priority from Japanese Patent Application No. 2007-249970, filed on Sep. 26, 2007, incorporated herein by reference.

BACKGROUND OF THE INVENTION

1. Field of the Invention

The present invention relates to a body-insertable apparatus system including a body-insertable apparatus to be inserted into a subject and a control unit that controls an operation of the body-insertable apparatus.

2. Description of the Related Art

In the field of endoscopes, swallow-type capsule endoscopes have been developed. This type of capsule endoscope has an imaging function and a wireless communication function. The capsule endoscope also has a function to move through insides of organs such as an esophagus, a stomach, and a small intestine due to their peristaltic movements and sequentially capture images after swallowed from a mouth of a patient to observe an inside of a body cavity until spontaneously excreted from a human body. An example of the capsule endoscope has been proposed in recent years that includes a needle coupled to a medical solution tank and an actuator that protrudes the needle, and that can inject the medical solution into a lesion area or the like (see, for example, Japanese Laid-open Patent Publication No. 2004-222998).

SUMMARY OF THE INVENTION

A body-insertable apparatus system according to an aspect of the present invention includes a body insertable apparatus that is inserted into a subject and a control apparatus that controls an operation of the body-insertable apparatus, wherein the body-insertable apparatus includes a magnetic responding unit that is provided within a casing forming the body-insertable apparatus and has a magnetization direction; and a needle that is protruded and retracted with respect to a surface of the casing, and the control apparatus includes a magnetic field generator that generates a magnetic field within the subject; and a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A wireless capsule inserting system, which is the best mode for carrying out the present invention (hereinafter, simply "embodiment"), is explained below with reference to the accompanying drawings. The present invention is not limited to the embodiment. In addition, in the description of the drawings, like parts are denoted by like reference letters or numerals.

First Embodiment

Figure 1:
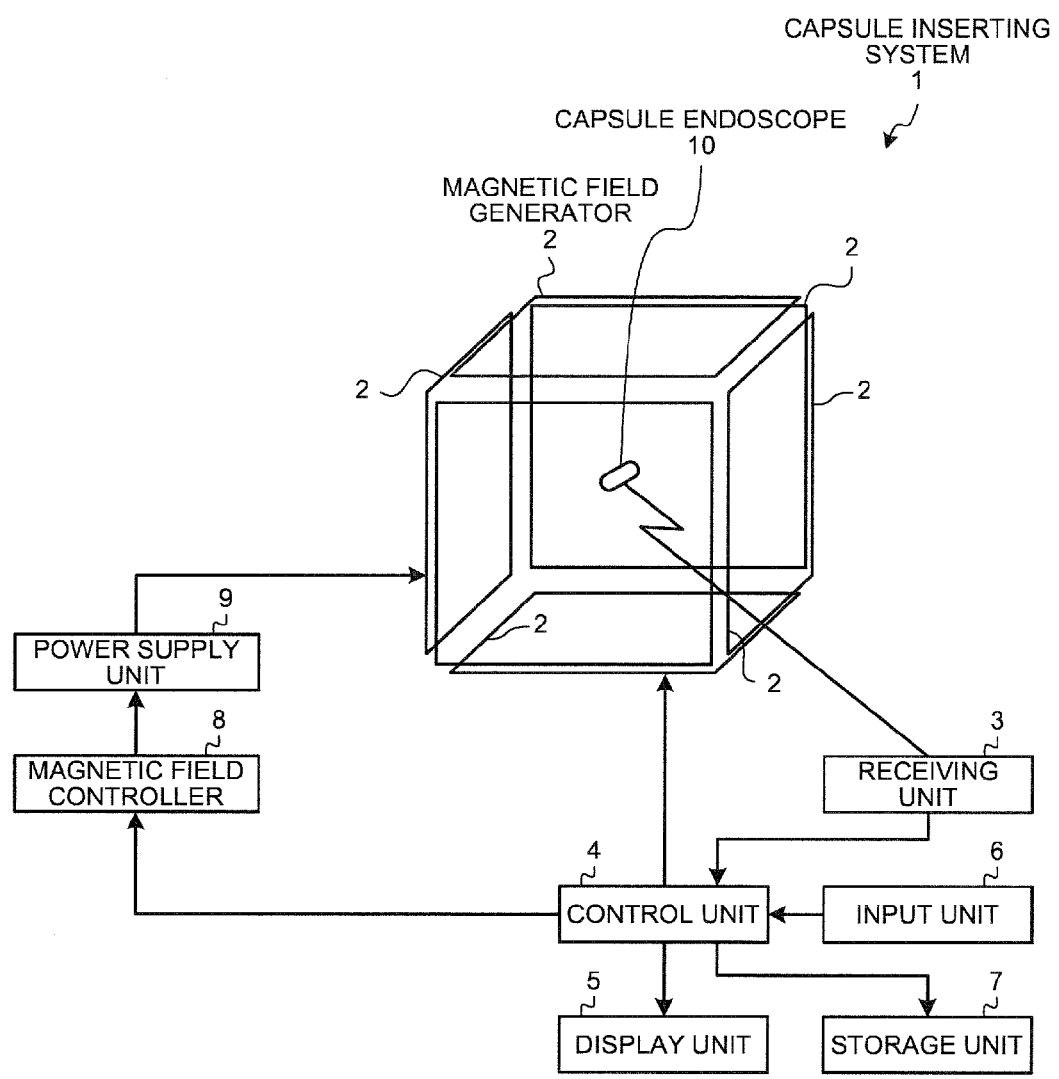
FIG. 1 is a schematic diagram of an overall configuration of a capsule inserting system according to a first embodiment.

A first embodiment is explained first. FIG. 1 is a schematic diagram of an overall configuration of a capsule inserting system according to the first embodiment. As shown in FIG. 1, a capsule inserting system 1 according to the first embodiment includes a capsule endoscope 10 of a capsule shape that is swallowed from a mouth of a subject to be inserted into a body cavity of the subject and communicate with external devices, a magnetic field generator 2 that is provided around the subject and can generate a three-dimensional rotating magnetic field, a receiving unit 3 that receives a wireless signal including images captured by the capsule endoscope 10 by establishing a wireless communication with the capsule endoscope 10, a control unit 4 that controls components of the capsule inserting system 1, a display unit 5 that displays the images captured by the capsule endoscope 10, an input unit 6 that inputs instruction information for instructing various operations in the capsule inserting system 1 to the control unit 4, a storage unit 7 that stores therein information of the images captured by the capsule endoscope 10 and the like, a magnetic field controller 8 that controls a magnetic field related to the magnetic field generator 2, and a power supply unit 9 that supplies power to the magnetic field generator 2 under control of the magnetic field controller 8. The receiving unit 3 detects a position and a posture of the capsule endoscope 10 within the subject based on a received strength of the signal transmitted from the capsule endoscope 10.

Figure 2:
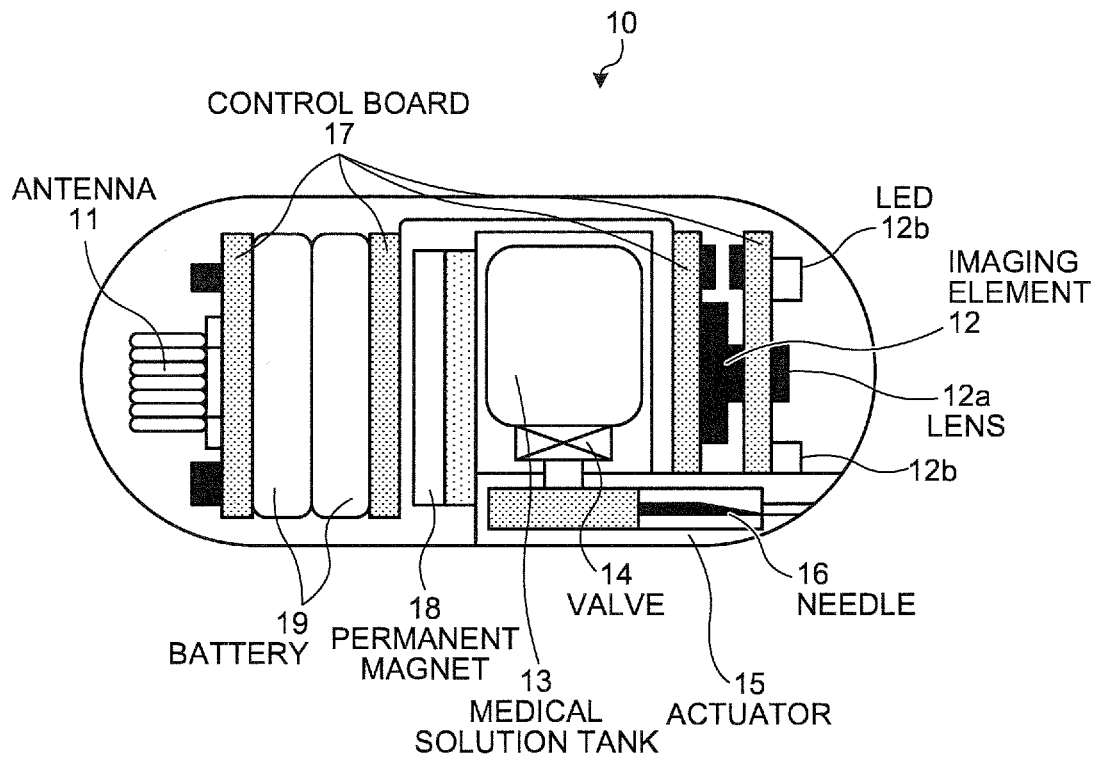
FIG. 2 is a schematic diagram of an internal configuration of a capsule endoscope shown in FIG. 1.
Figure 3:
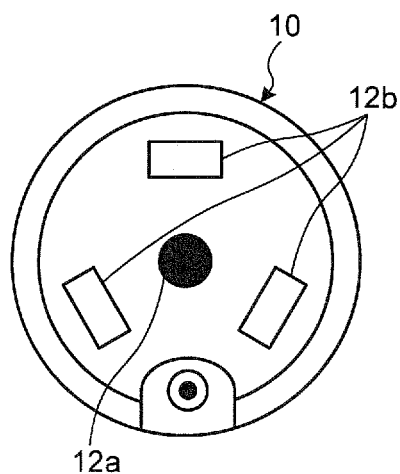
FIG. 3 is a right side view of the capsule endoscope shown in FIG. 2.
Figure 4:
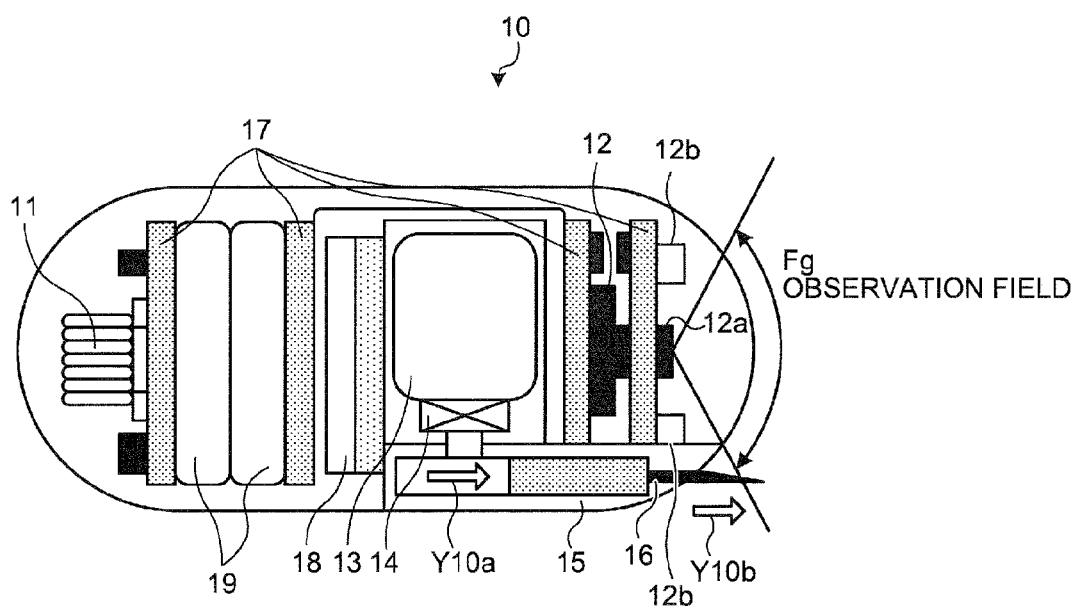
FIG. 4 is a schematic diagram of the internal configuration of the capsule endoscope shown in FIG. 1.

The capsule endoscope 10 shown in FIG. 1 is explained next. FIGS. 2 and 4 are schematic diagrams of an internal configuration of the capsule endoscope 10 shown in FIG. 1. FIG. 3 is a right side view of the capsule endoscope 10 shown in FIG. 2. As shown in FIG. 2, the capsule endoscope 10 includes an antenna 11 that transmits a wireless signal to the receiving unit 3, a lens 12a that focuses reflected light, an LED 12b that irradiates an observation field Fg with light, an imaging element 12 that captures images of an inside of a body cavity of a subject, a medical solution tank 13 that has a medical solution stored therein to be injected to a predetermined site in the subject, a valve 14 for opening and closing an opening of the medical solution tank 13 by driving a driving member (not shown), an actuator 15 that houses a motor and the like, a needle 16 for injecting the medical solution stored in the medical solution tank 13 into a desired site in the subject, a control board 17 on which a control circuit that controls the components of the capsule endoscope 10 in accordance with the wireless signal received by the antenna 11 from the receiving unit 3 is provided, a permanent magnet 18, and a battery 19 that supplies power to the components of the capsule endoscope 10. The needle 16 can be protruded from or retracted within a surface of a casing of the capsule endoscope 10. The permanent magnet 18 is provided within the capsule endoscope 10 to have a magnetization direction approximately parallel to a long axis direction of the casing of the capsule endoscope 10. As shown in FIG. 3, a distal end of the casing of the capsule endoscope 10 on the side of the imaging element 12 is made of a transparent member so that the observation field Fg can be irradiated with the light from the LED 12b.

The actuator 15 is connected to a rear end of the needle 16. The actuator 15 can be moved, for example, in a horizontal direction in FIG. 2 under control of the control board 17. Accordingly, when the actuator 15 is moved from a state shown in FIG. 2 to the right in FIG. 4 as shown by an arrow Y10a in FIG. 4, the needle 16 is moved to the right due to the motion of the actuator 15 as shown by an arrow Y10b in FIG. 4 and protrudes outside the capsule endoscope 10. An installation position of the needle 16 in the capsule endoscope 10, an installation position of the lens 12a, a focusing efficiency of the lens 12a, an irradiation range of the LED 12b, and the like are set so that a distal end of the needle 16 enters the observation field Fg when the needle 16 protrudes outside the capsule endoscope 10. Accordingly, a user of the capsule inserting system 1 can determine whether the needle 16 protrudes outside the capsule endoscope 10 and can check a puncture state of the needle and a state of injection of the medical solution, by checking the images captured by the imaging element 12 and displayed on the display unit 5.

When the actuator 15 is moved to the left in FIG. 4 from the state shown in FIG. 4, the needle 16 is moved to the left due to the motion of the actuator 15 and retracted in the capsule endoscope 10. In this way, the actuator 15 and the control board 17 have a function to enable the needle 16 to perform a protruding operation and a retracting operation. The needle 16 is provided within the capsule endoscope 10 such that a distal end direction of the protruded needle 16 is approximately parallel to the long axis direction of the capsule endoscope 10 as shown in FIGS. 2 and 4. Accordingly, the needle 16 is protruded or retracted approximately in parallel to the long axis direction of the capsule endoscope 10. The distal end direction of the protruded needle 16 is approximately parallel to the magnetization direction of the permanent magnet 18. The actuator 15 is moved using the power supplied from the battery 19.

Figure 5:
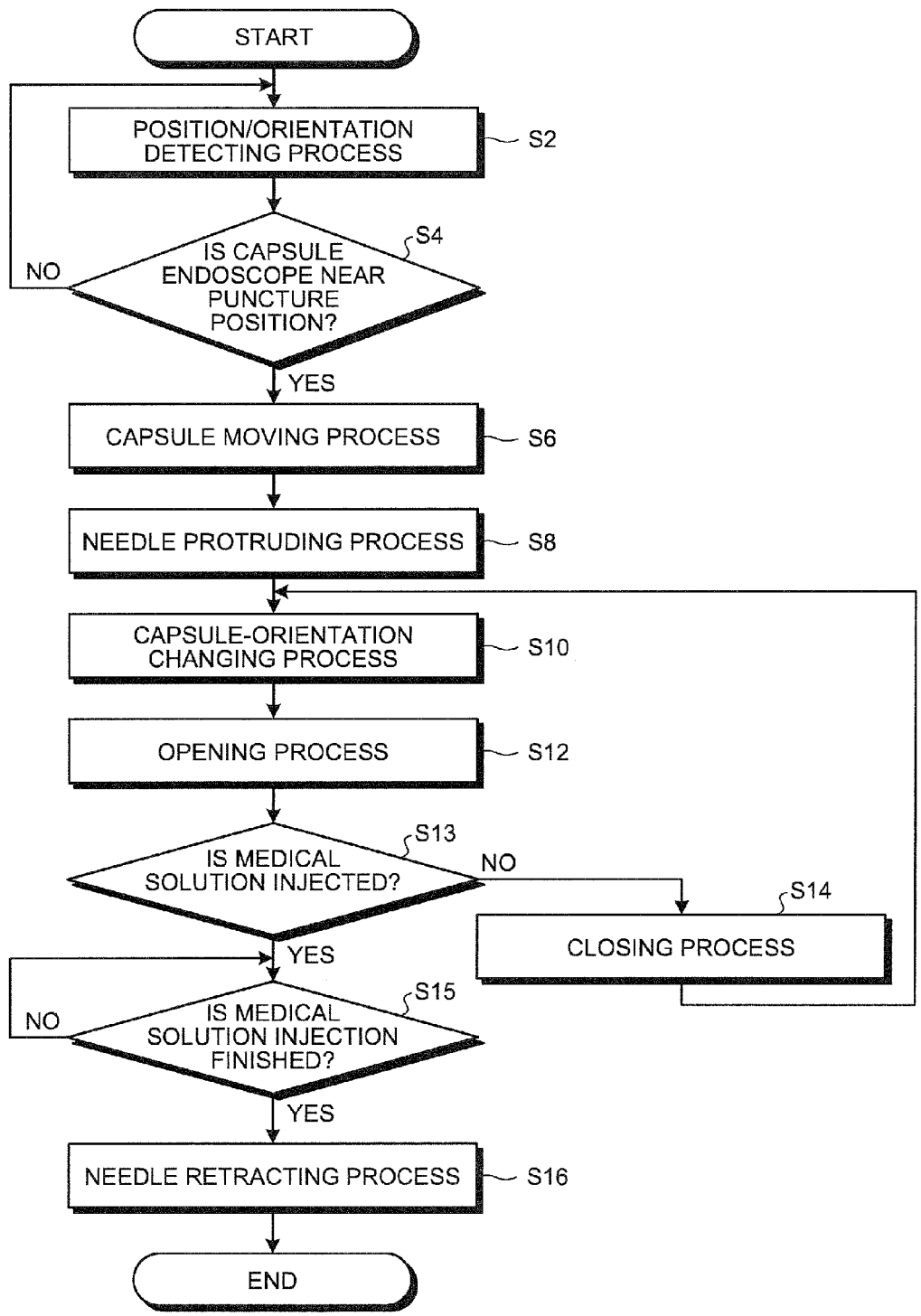
FIG. 5 is a flowchart of a process procedure explaining a medical-solution injecting process performed by the capsule inserting system 1 shown in FIG. 1.

A medical-solution injecting process performed by the capsule inserting system 1 shown in FIG. 1 is explained next with reference to FIG. 5. FIG. 5 is a flowchart of a process procedure explaining a medical-solution injecting process performed by the capsule inserting system 1 shown in FIG. 1.

In the capsule inserting system 1 shown in FIG. 1, the capsule endoscope 10 is first ingested into a subject and then a communicating process between the capsule endoscope 10 and the receiving unit 3 is started. The receiving unit 3 processes a wireless signal transmitted from the capsule endoscope 10 and sequentially outputs image information including images captured by the capsule endoscope 10 to the control unit 4. The display unit 5 sequentially displays the images captured by the capsule endoscope 10 under control of the control unit 4. In this case, the receiving unit 3 processes the wireless signal transmitted from the capsule endoscope 10 to output the images captured by the capsule endoscope 10, and also performs a position/orientation detecting process for detecting a position and an orientation of the capsule endoscope 10 in the subject based on a received strength of each wireless signal transmitted from the capsule endoscope 10 (Step S2). A result of the position/orientation detecting process performed by the receiving unit 3 is outputted to the control unit 4, and the display unit 5 displays the images under control of the control unit 4 and also displays the position and the orientation of the capsule endoscope 10 at the time of capture of the displayed images. The imaging process of the capsule endoscope 10 and the image display of the display unit 5 can be regarded as being performed almost in real-time, and therefore the user of the capsule inserting system 1 can give a diagnosis or instruct injection of the medical solution assuming that the capsule endoscope 10 is located at the position where the images displayed on the display unit 5 are captured.

The control unit 4 then determines whether instruction information indicating that the capsule endoscope 10 is near a puncture position is received from the input unit 6 (Step S4). When determining that the capsule endoscope 10 is near a position to be punctured by the needle 16 by checking the images displayed on the display unit 5 and the position and orientation of the capsule endoscope 10, the user of the capsule endoscope 10 operates the input unit 6 to input the instruction information indicating that the capsule endoscope 10 is near the puncture position. When the control unit 4 determines that the instruction information indicating that the capsule endoscope 10 is near the puncture position is not received from the input unit 6 (NO at Step S4), the receiving unit 3 performs the position/orientation detecting process for the capsule endoscope 10 again (Step S2).

In contrast, when the control unit 4 determines that the instruction information indicating that the capsule endoscope 10 is near the puncture position is received from the input unit 6 (YES at Step S4), the capsule inserting system 1 performs a capsule moving process for moving the capsule endoscope 10 and changing an orientation thereof to cause the capsule endoscope 10 to have a desired posture to be taken by the capsule endoscope 10 immediately before puncture of the needle 16 based on the instruction information from the input unit 6 (Step S6). Specifically, the user operates the input unit 6 to input instruction information for instructing a position to which the capsule endoscope 10 is to be moved and a posture taken by the capsule endoscope 10. The input unit 6 inputs the instruction information for instructing the position to which the capsule endoscope 10 is to be moved and the posture taken by the capsule endoscope 10 to the control unit 4. The magnetic field controller 8 causes the magnetic field generator 2 to generate a magnetic field for changing a position and an orientation of the permanent magnet 18 in the capsule endoscope 10 in accordance with the instruction information inputted through the control unit 4 so that the capsule endoscope 10 has the desired posture to be taken immediately before puncture of the needle 16. In this case, the magnetic field controller 8 causes the magnetic field generator 2 to generate the magnetic field for changing the position and orientation of the permanent magnet 18 in the capsule endoscope 10 based on the magnetization direction of the permanent magnet 18 in the capsule endoscope 10, a position of the needle 16 in the capsule endoscope 10, and a distal end direction of the needle 16. The magnetic field controller 8 causes the magnetic field generator 2 to generate the magnetic field with intensity sufficient for the capsule endoscope 10 to change the position and the orientation. In this way, the control unit 4 changes the orientation and position of the entire capsule endoscope 10 to have the desired posture to be taken immediately before puncture of the needle 16.

The capsule inserting system 1 then performs a needle protruding process for protruding the needle 16 in the capsule endoscope 10 (Step S8). Specifically, the user operates the input unit 6 to input instruction information for instructing needle protrusion. The input unit 6 inputs the instruction information for instructing the needle protrusion to the control unit 4, and the receiving unit 3 transmits a wireless signal instructing the needle protrusion to the capsule endoscope 10 under control of the control unit 4. In the capsule endoscope 10, the antenna 11 receives the wireless signal instructing the needle protrusion transmitted from the receiving unit 3, and the actuator 15 operates in accordance with the instruction signal received by the antenna 11 under control of the control board 17 to protrude the needle 16 outside the capsule endoscope 10.

The capsule inserting system 1 then performs a capsule-orientation changing process for changing an orientation of the entire capsule endoscope 10 so that the protruded needle 16 can puncture a puncture target layer (Step S10). Specifically, the user operates the input unit 6 to input instruction information for instructing an orientation in which the capsule endoscope 10 is to be changed to the control unit 4. The input unit 6 inputs instruction information for instructing the changed orientation of the capsule endoscope 10 to the control unit 4. The magnetic field controller 8 causes the magnetic field generator 2 to generate a magnetic field for changing the orientation of the permanent magnet 18 in the capsule endoscope 10 in accordance with the instruction information inputted through the control unit 4. In this case, the magnetic field controller 8 causes the magnetic field generator 2 to generate a magnetic field for changing the orientation of the permanent magnet 18 in the capsule endoscope 10 based on the magnetization direction of the permanent magnet 18 in the capsule endoscope 10, the position of the needle 16 in the capsule endoscope 10, and the distal end direction of the needle 16. As a result, the orientation of the entire capsule endoscope 10 can be changed due to the change in the orientation of the permanent magnet 18. In this way, the capsule inserting system 1 changes the orientation of the entire capsule endoscope 10 to enable the protruded needle 16 to puncture the puncture target layer, so that the needle 16 can puncture the puncture target layer.

The capsule inserting system 1 then performs an opening process for opening the medical solution tank 13 in the capsule endoscope 10 (Step S12) to inject the medical solution in the medical solution tank 13 into a target region through the needle 16. Specifically, the user operates the input unit 6 to input instruction information for instructing medical solution injection. The input unit 6 inputs the instruction information for instructing the medical solution injection to the control unit 4, and the receiving unit 3 transmits a wireless signal to instruct an opening operation for the valve 14 to the capsule endoscope 10 under control of the control unit 4. In the capsule endoscope 10, the valve 14 is opened in accordance with the received wireless signal, and consequently the medical solution in the medical solution tank 13 is injected into the target region through the needle 16.

The control unit 4 then determines whether the medical solution in the medical solution tank 13 is injected (Step S13). When it is determined that the medical solution in the medical solution tank 13 is not injected (NO at Step S13), a closing process for closing the medical solution tank 13 in the capsule endoscope 10 is performed (Step S14) and then the processing is returned to Step S10 to perform the capsule-orientation changing process. When the medical solution is not injected to an intestine wall or the like as a target for the medical solution injection, the medical solution tank 13 in the capsule endoscope 10 is once closed and then the process for changing the orientation of the capsule endoscope 10 is performed again, which realizes more reliable injection. When determining that the medical solution in the medical solution tank 13 is injected (YES at Step S13), the control unit 4 determines whether the medical solution injection is finished based on an injection time for the medical solution or the like (Step S15). When determining that the medical solution injection is not finished (NO at Step S15), the control unit 4 repeats the process at Step S15. That is, the control unit 4 repeats the determining process at Step S15 until it is determined that the medical solution injection is finished. When determining that the medical solution injection is finished (YES at Step S15), the control unit 4 performs a needle retracting process for closing the valve 14 and retracting the protruded needle 16 into the capsule endoscope 10 (Step S16). Specifically, the receiving unit 3 transmits a wireless signal to instruct a closing operation for the valve 14 and needle retraction to the capsule endoscope 10. In the capsule endoscope 10, the valve 14 is closed in accordance with the received wireless signal. The actuator 15 then operates under control of the control board 17 to retract the needle 16 within the capsule endoscope 10. In this way, the process for injecting the medical solution is performed in the capsule inserting system 1.

Figure 6:
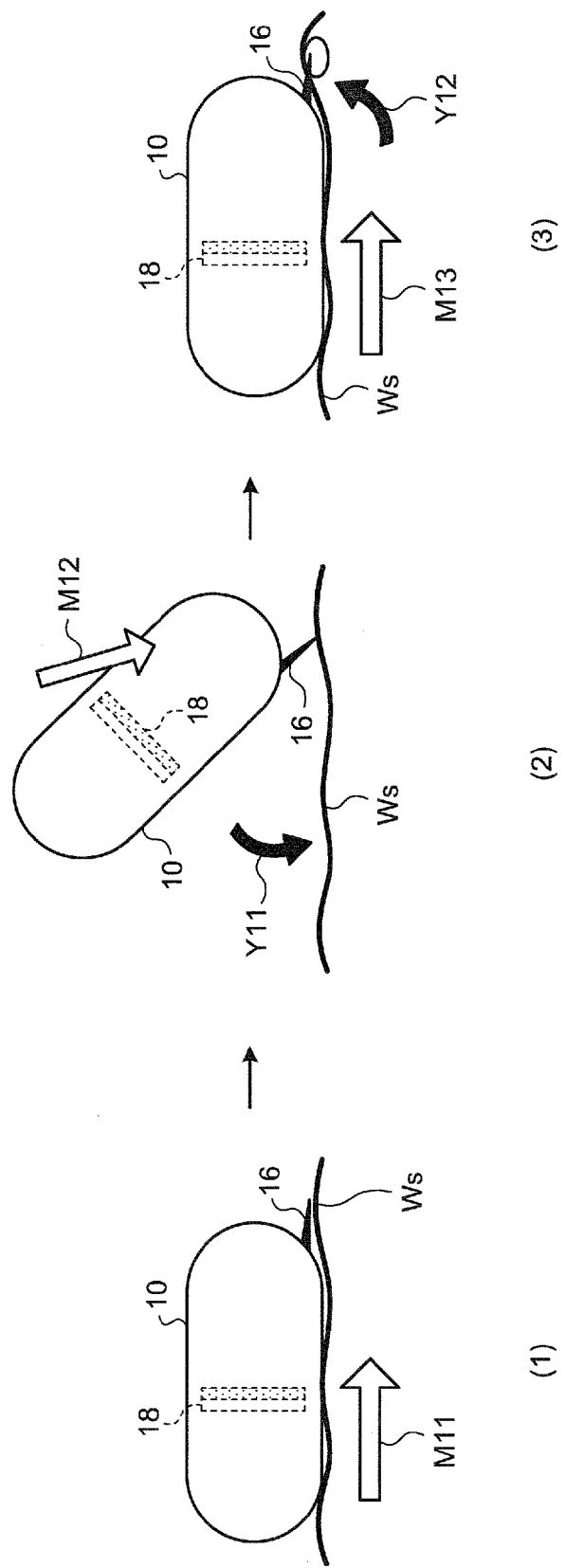
FIG. 6 is an explanatory diagram of an orientation changing process for the capsule endoscope shown in FIG. 2.

The capsule-orientation changing process shown in FIG. 5 is explained next in detail. FIG. 6 is a schematic diagram explaining the orientation changing process for the capsule endoscope 10 shown in FIGS. 2 to 4, and depict an example of a space, such as a stomach, which is wider in a vertical direction than a length of the capsule endoscope 10 in the long axis direction. As shown in FIG. 6(1), the magnetic field generator 2 applies a magnetic field M11 in a direction parallel to a surface of a stomach wall Ws to the capsule endoscope 10 to place the capsule endoscope 10 on the stomach wall Ws in a desired posture to be taken immediately before puncture.

Thereafter, in the capsule endoscope 10, the needle 16 is protruded as shown in FIG. 6(1). The magnetic field generator 2 changes the direction of the magnetic field applied to the capsule endoscope 10 obliquely to orient the distal end of the protruded needle 16 toward the stomach wall Ws as shown by a magnetic field M12 in FIG. 6(2). As a result, the orientation of the permanent magnet 18 in the capsule endoscope 10 changes to a direction inclined with respect to the stomach wall Ws in accordance with a magnetic field direction of the magnetic field M12. With inclination of the permanent magnet 18, the orientation of the entire capsule endoscope 10 is also inclined and the rear end of the capsule endoscope 10 is lifted from the stomach wall Ws. In this case, an almost entire weight of the capsule endoscope 10 is put on the distal end of the needle 16 oriented toward the stomach wall Ws and thus large force is applied in the distal end direction of the needle 16. Accordingly, the needle 16 punctures the stomach wall Ws.

As shown by an arrow Y11 in FIG. 6(2), the direction of the inclined magnetic field M12 is brought back as shown by a magnetic field M13 in FIG. 6(3) so that the long axis direction of the capsule endoscope 10 and the surface of the stomach wall Ws are parallel to each other. As a result, the orientation of the permanent magnet 18 in the capsule endoscope 10 changes to be approximately parallel to the stomach wall Ws as shown in FIG. 6(3), and the orientation of the capsule endoscope 10 is changed in accordance with the orientation change of the permanent magnet 18 so that the long axis direction of the capsule endoscope 10 is approximately parallel to the stomach wall Ws. The orientation of the needle 16 stuck in the stomach wall Ws is also changed to be approximately parallel to the stomach wall Ws. The change in the orientation of the needle 16 enables an action of the needle 16 like scooping of the stomach wall Ws as shown by an arrow Y12 in FIG. 6(3), so that the needle 16 can be stuck in the stomach wall Ws more reliably. The valve 14 is then opened and the medical solution in the medical solution tank 13 is injected into the stomach wall Ws.

Figure 7:
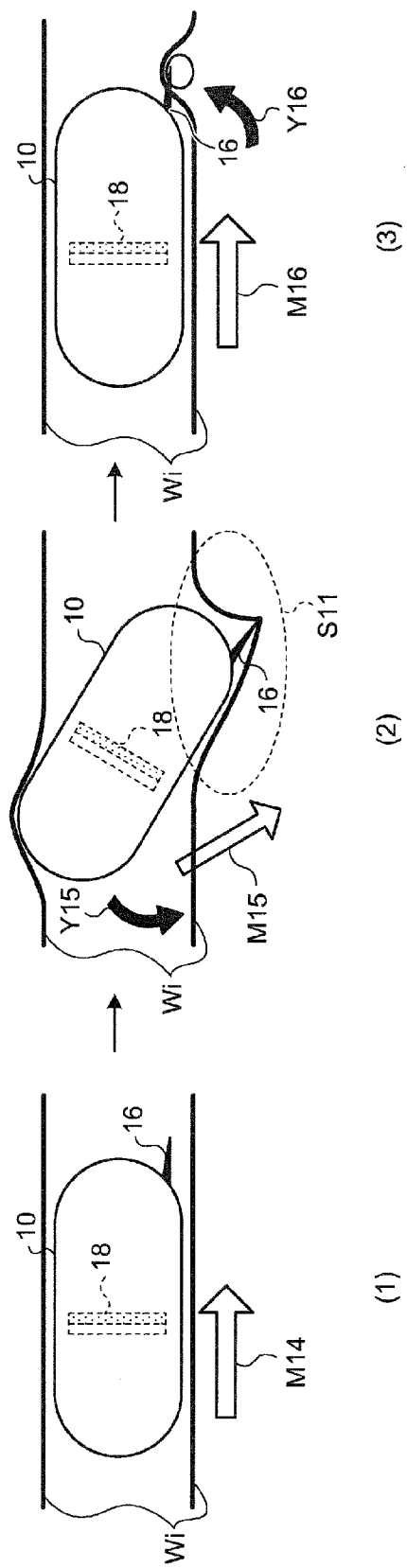
FIG. 7 is an explanatory diagram of an orientation changing process for the capsule endoscope shown in FIG. 2.

An example of a narrow space, such as a small intestine, having an inside diameter similar to an outside diameter of the capsule endoscope 10 is explained with reference to FIG. 7. In this case, like in FIG. 6(1), the magnetic field generator 2 applies a magnetic field M14 having a direction parallel to a surface of an intestine wall Wi to the capsule endoscope 10 as shown in FIG. 7(1), to place the capsule endoscope 10 on the intestine wall Wi in a desired posture to be taken immediately before puncture. In the capsule endoscope 10, the needle 16 is then protruded. As shown by a magnetic field M15 in FIG. 7(2), the magnetic field generator 2 obliquely changes the direction of the magnetic field to orient the distal end of the protruded needle toward the intestine wall Wi. As a result, the orientation of the permanent magnet 18 in the capsule endoscope 10 is changed to be inclined in accordance with the magnetic field direction of the magnetic field M15, and the orientation of the entire capsule endoscope 10 is also inclined. Tension is applied to the intestine wall Wi by the inclined capsule endoscope 10 to expand the intestine wall Wi, and the needle 16 is brought in contact with the intestine wall Wi expanded as shown by a region S11. In this case, elastic force (reaction force) of the intestine wall is put on the distal end of the inclined needle 16, and thus large force is applied in the distal end direction of the needle 16. Accordingly, the needle 16 punctures the intestine wall Wi. When the needle 16 is further inclined toward a direction of gravitational force, weights of the capsule endoscope 10 and the intestine wall can be put on the distal end of the needle 16.

As shown by an arrow Y15 in FIG. 7(2), the direction of the inclined magnetic field M15 is then brought back as shown by a magnetic field M16 in FIG. 7(3) so that the capsule endoscope 10 is parallel to the intestine wall Wi. As a result, the orientation of the permanent magnet 18 in the capsule endoscope 10 is changed to be approximately parallel to the intestine wall Wi as shown in FIG. 7(3), and the orientation of the capsule endoscope 10 is turned back. The orientation of the needle 16 stuck in the intestine wall Wi is also changed to be approximately parallel to the intestine wall Wi. The change in the orientation of the needle 16 enables an action of the needle 16 like scooping of the intestine wall Wi as shown by an arrow Y16 in FIG. 7(3), and accordingly the needle 16 can puncture the intestine wall Wi more reliably. The valve 14 is then opened and the medical solution in the medical solution tank 13 is injected into the intestine wall Wi.

As described above, in the first embodiment, the direction of the magnetic field applied to the permanent magnet 18 is changed to change the orientation of the entire capsule endoscope 10, thereby providing a large motion to the needle 16. Accordingly, the needle 16 can be reliably stuck in the puncture target layer. In the first embodiment, the long axis direction (direction of observation) of the capsule endoscope 10 and the magnetization direction of the permanent magnet 18 in the capsule endoscope 10 are the same. Therefore, the long axis direction of the capsule endoscope 10 can be changed to a direction of the magnetic direction applied, and thus the long axis direction of the capsule endoscope 10 can be uniquely determined with respect to the generated magnetic field. Further, in the first embodiment, the distal end direction of the needle 16 and the magnetization direction are approximately parallel to each other. Therefore, the needle 16 can puncture in the direction of the applied magnetic direction, and accordingly the direction of the puncture can be uniquely determined.

The user may instruct the direction of the magnetic field to be changed while viewing in-vivo images of the subject displayed on the display unit 5 or based on the result of the position and orientation detection for the capsule endoscope 10 from the receiving unit 3. When instructing the orientation of the capsule endoscope 10 while viewing the subject images, the user may apply the magnetic field without the needle 16 protruded. After checking the direction of a magnetic field to be actually generated, the user can protrude the needle 16 and then instruct magnetic field application.

In a wide space such as a stomach, there is naturally an open space vertically above the capsule endoscope 10. In such a case, the capsule endoscope 10 is placed on the stomach wall Ws stably in a position where the stomach wall Ws has a small inclination (is nearly horizontal) with the long axis direction approximately parallel to the surface of the stomach wall Ws. Accordingly, it is considered that, when a magnetic field in a vertical direction is applied, the permanent magnet 18 stands up so that the magnetization direction of the permanent magnet 18 becomes vertical, and also the capsule endoscope 10 certainly stands up in response thereto. Therefore, it is only required that the user instructs a vertical magnetic field in order to stand the capsule endoscope 10 up.

In a narrow space such as a small intestine, it is also possible to protrude the needle 16 after the inclined magnetic field M15 is applied as shown in FIG. 7(2) and the tension generated by inclination of the capsule endoscope 10 is put on the intestine wall Wi to sufficiently expand the intestine wall Wi. When the capsule endoscope 10 is inclined after the needle 16 is previously protruded, the needle 16 may be pushed back into the capsule endoscope 10 due to an amount of inclining motion of the capsule endoscope 10 or rebound of the intestine wall Wi. Therefore, it is considered that the needle 16 can be stuck in the intestine wall Wi more reliably when the needle 16 is protruded after the capsule endoscope 10 is inclined to expand the intestine wall Wi.

In the first embodiment, the examples in which the direction of the magnetic field applied by the magnetic field generator 2 is changed to change the orientation of the capsule endoscope 10 as shown in FIGS. 6(2) and 6(3) and FIGS. 7(2) and 7(3) are explained. The present invention is not limited thereto. For example, the magnetic field controller 8 stops the application of the magnetic field M12 or M15 applied to incline the capsule endoscope 10, thereby zeroing the generated magnetic field. In this case, the inclined capsule endoscope 10 falls down on the stomach wall Ws or Wi due to the weight of the capsule endoscope 10, and consequently the needle 16 having the distal end in contact with the stomach wall Ws or Wi is moved like scooping and reliably punctures the stomach wall Ws or Wi. Thus, the orientation of the permanent magnet 18 can be changed by changing the intensity of the magnetic field generated by the magnetic field generator 2, so that the orientation of the entire capsule endoscope 10 can be changed.

The needle 16 may be provided in such a manner that the distal end direction of the needle 16 when protruded is different from the direction of protrusion or retraction of the needle 16. In this way, effects of the reaction force from the intestine wall or the like on the actuator 15 during puncture of the needle 16 can be reduced.

Figure 8:
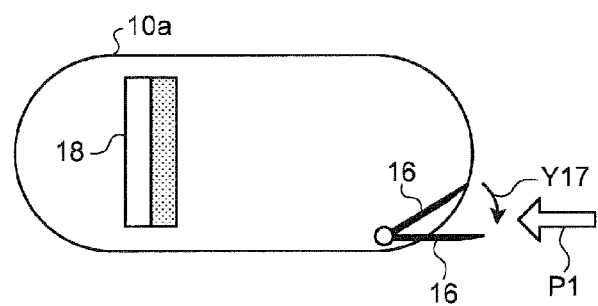
FIG. 8 is a schematic diagram of another example of the internal configuration of the capsule endoscope shown in FIG. 1.

Specifically, as shown by a capsule endoscope 10a in FIG. 8, the distal end direction of the needle 16 when protruded is made approximately parallel to a long axis direction of the capsule endoscope 10a. The needle 16 is adapted to protrude outside the capsule endoscope 10a in a protruding direction different from the long axis direction of the capsule endoscope 10a, as shown by an arrow Y17.

When the entire capsule endoscope 10a is inclined by application of an inclined magnetic field like in the case shown in FIG. 6(2) or 7(2), reaction force P1 transmitted back from the intestine wall against tension from the capsule endoscope 10a is applied to the capsule endoscope 10a. The reaction force P1 is transmitted back in a direction parallel to the long axis direction of the capsule endoscope 10a against the direction of the inclined magnetic field. In the capsule endoscope 10 shown in FIGS. 2 to 4, the actuator 15 is adapted to move the needle 16 approximately in parallel to the long axis direction of the capsule endoscope 10. Therefore, when the reaction force P1 in the same direction as the retraction direction of the needle 16 as shown in FIG. 8 is applied, the protruded needle 16 is sometimes pushed back into the capsule endoscope 10 due to the reaction force P1. In contrast, in the capsule endoscope 10a, even when the reaction force P1 in the same direction as the distal end direction of the needle 16 is applied for example, effects of the reaction force P1 are smaller than those in the case where the distal end direction of the needle 16 and the protrusion direction of the needle 16 are the same, because the direction of protrusion or retraction of the needle 16 is different from that of the reaction force P1. Accordingly, the needle 16 is not pushed back. Therefore, the needle 16 can be properly stuck in the puncture target layer.

Figure 9:
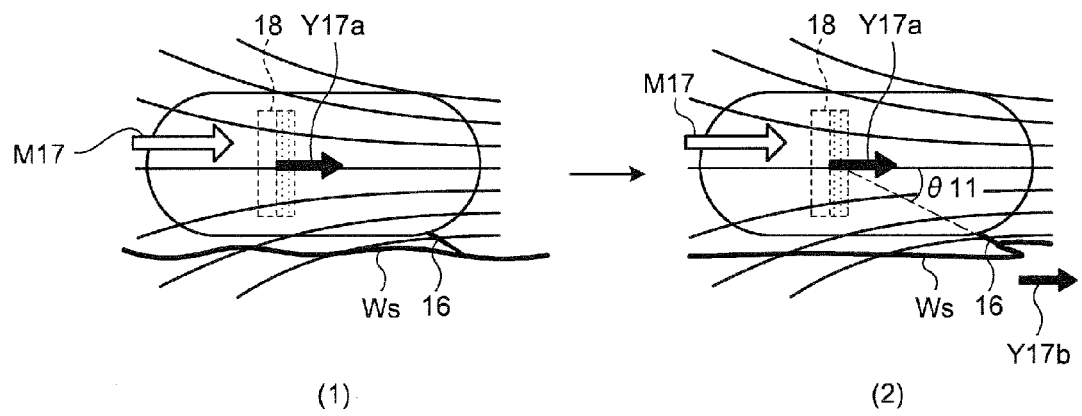
FIG. 9 is an explanatory diagram of an orientation changing process for the capsule endoscope according to the first embodiment.

The magnetic field generator 2 may generate magnetic attracting force in the magnetic field direction by changing a magnetic flux density of the magnetic field M12 or M15 to the magnetic field direction when the needle 16 is stuck in the stomach wall Ws or the intestine wall Wi in FIGS. 6(2) and 6(3) or FIGS. 7(2) and 7(3) under control of the magnetic field controller 8. In this case, the magnetization direction of the permanent magnet 18 and the distal end direction of the needle 16 are approximately parallel to each other, and the permanent magnet 18 is moved in the magnetic field direction by the magnetic attracting force. Accordingly, the needle 16 receives force to be pressed hard against the intestine wall Wi or Ws by the magnetic attracting force and is reliably stuck in the stomach wall Ws. Of course, also in a case where the distal end direction of the needle 16 and the magnetization direction of the permanent magnet 18 are not strictly parallel to each other as shown in FIG. 9(1), the magnetic field generator 2 can apply a gradient magnetic field M17 having a magnetic flux density changed in the magnetic field direction to the permanent magnet 18 under control of the magnetic field controller 8 to generate magnetic attracting force in a direction shown by an arrow Y17a, so that the needle 16 is pressed hard against the stomach wall Ws due to movement of the entire capsule endoscope in the direction shown by the arrow Y17a. When the distal end direction of the needle 16 and the magnetization direction of the permanent magnet 18 are not parallel to each other as in the case shown in FIG. 9, an angle θ11 formed by the distal end direction of the needle 16 and the magnetization direction of the permanent magnet 18 shown in FIG. 9(2) needs to be equal to or smaller than 45° to apply the magnetic attracting force parallel to the magnetization direction of the permanent magnet 18 to the puncture direction of the needle 16. When the angle θ11 is equal to or smaller than 45°, the magnetic attracting force in the direction shown by the arrow Y17a can be applied in the puncture direction of the needle 16 as shown in FIG. 9(2). Therefore, the needle 16 is pressed against the stomach wall Ws by the magnetic attracting force as shown by an arrow Y17b and therefore can be reliably stuck. When the angle θ11 is equal to or smaller than 30°, 80% or more of components of the magnetic attracting force can be applied in the puncture direction of the needle 16. Therefore, it is desirable that the angle θ11 be equal to or smaller than 30°.

Figure 10:
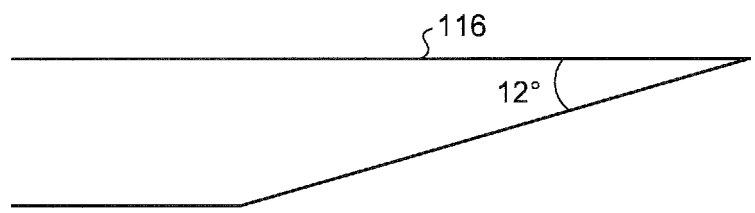
FIG. 10 is an explanatory diagram of a needle included in a capsule endoscope according to a conventional technique.
Figure 11:
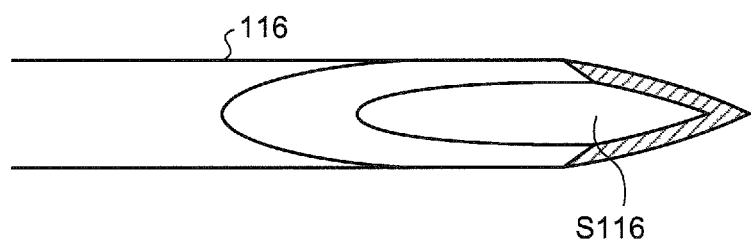
FIG. 11 is an explanatory diagram of the needle included in the capsule endoscope according to the conventional technique.
Figure 12:
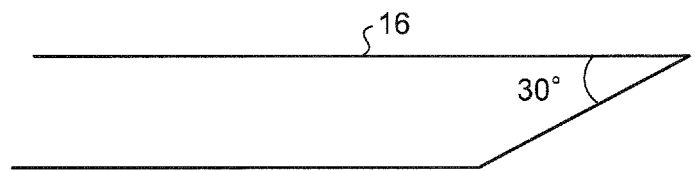
FIG. 12 is an explanatory diagram of a needle included in the capsule endoscope according to the first embodiment.

A normal injection needle generally has a distal end sharpened by cutting the distal end in two stages at acute angles to be stuck deeply. For example, the distal end of the needle 16 is first cut at about 12° as shown in FIG. 10 and then cut at an angle of 15° obliquely with respect to a cut surface as shown in FIG. 11. In the capsule endoscope, however, it is unnecessary to stick the needle as deeply as in the normal injection needle because the intestine wall or the stomach wall is a puncture target layer. In the capsule endoscope, it is required that the needle be reliably stuck selectively in a puncture target layer with a predetermined thickness. For this purpose, the distal end of the needle 16 is cut at an angle of about 30°, which is larger than that of the normal injection needle, to reliably stick the needle 16 selectively in the puncture target layer as shown in FIGS. 12 and 13.

Figure 13:
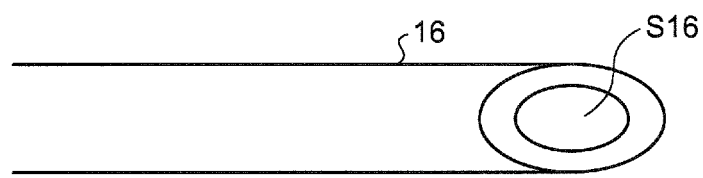
FIG. 13 is an explanatory diagram of the needle included in the capsule endoscope according to the first embodiment.
Figure 14:
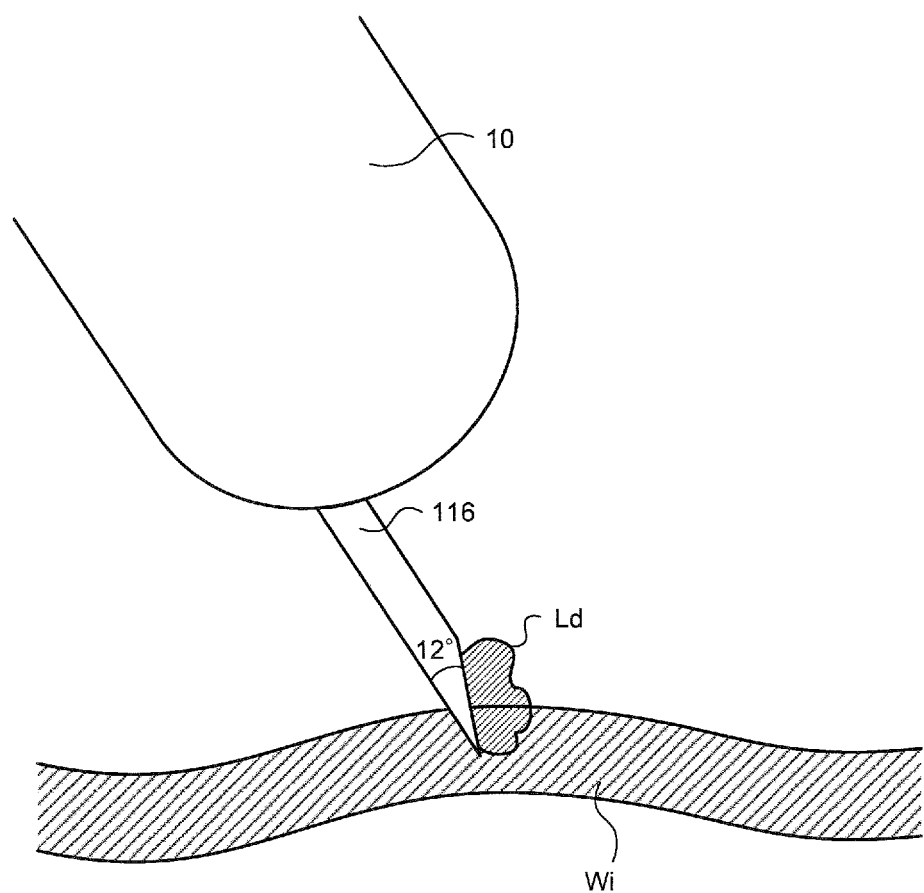
FIG. 14 is an explanatory diagram of the needle included in the capsule endoscope according to the conventional technique.

As shown by an area S116 of a discharge opening of a needle 116 shown in FIG. 11, when the distal end is cut at acute angles in two stages like the normal injection needle, a discharge opening thereof has a larger area than an area S16 of a discharge opening of the needle 16 cut at the angle of about 30° in FIG. 13. Further, when the needle 116 is stuck in the intestine wall Wi as the puncture target layer so that the cut surface is substantially perpendicular to the surface of the puncture target layer as shown in FIG. 14, there are cases where only part of the discharge opening is stuck in the puncture target layer because the discharge opening area is large. In such cases, the medical solution is spilled out through a part not stuck in the puncture target layer, and accordingly the medical solution cannot be properly injected into the puncture target layer.

Figure 15:
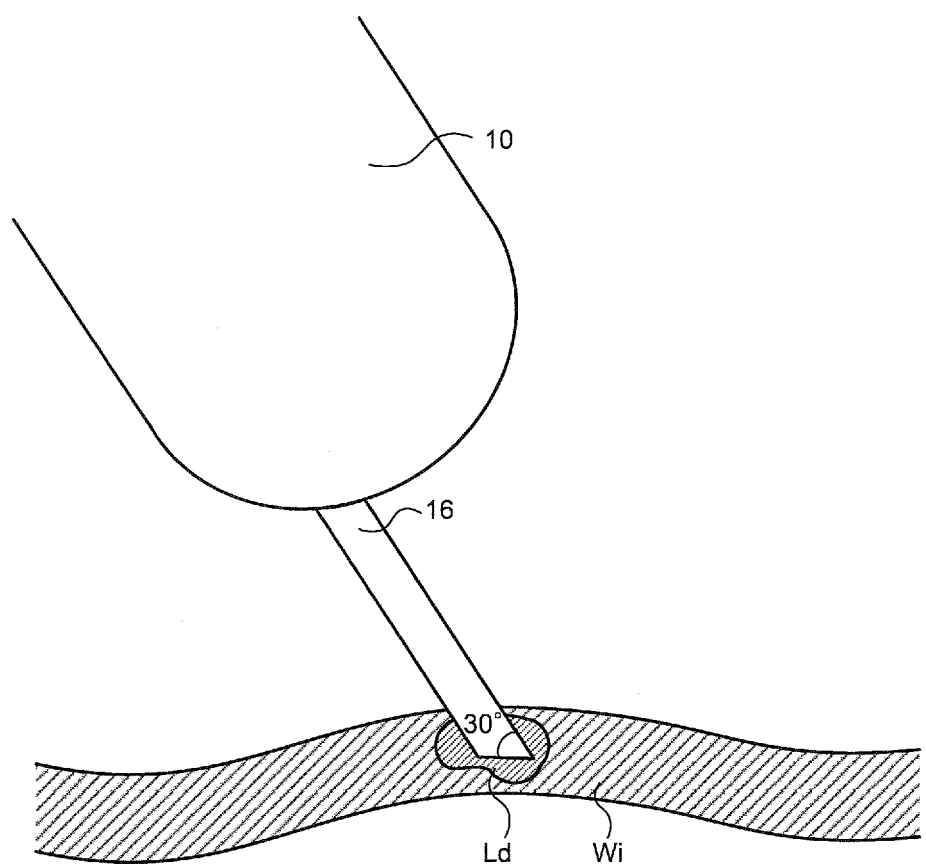
FIG. 15 is an explanatory diagram of the needle included in the capsule endoscope according to the first embodiment.

To solve an injection failure for a medical solution Ld, the needle 16 is provided in the casing of the capsule endoscope to make the cut surface of the needle 16 approximately parallel to the surface of the puncture target layer, as shown in FIG. 15. Because the needle 16 is cut at a larger angle than that of a conventional injection needle, the needle 16 is adapted to have a discharge opening area that can properly puncture the puncture target layer. In addition, because the needle 16 is provided in the casing of the capsule endoscope so that the cut surface of the needle 16 is approximately parallel to the surface of the puncture target layer, the entire discharge opening of the cut surface can be stuck in the puncture target layer. Accordingly, the medical solution Ld can be properly injected into the puncture target layer. To provide the needle 16 in the casing of the capsule endoscope so that the cut surface of the needle 16 is approximately parallel to the surface of the puncture target layer, the cut surface of the needle 16 is oriented toward an outer side of the capsule endoscope 10 or 10a.

Second Embodiment

Figure 16:
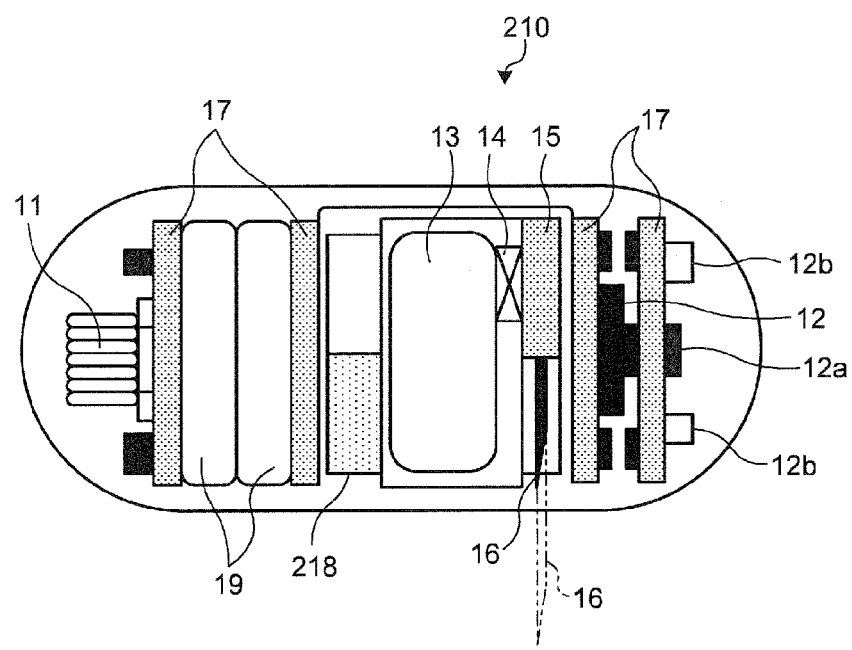
FIG. 16 is a schematic diagram of an internal configuration of a capsule endoscope according to a second embodiment.

A second embodiment is explained next. FIG. 16 depicts an internal configuration of a capsule endoscope according to the second embodiment. A capsule inserting system according to the second embodiment has a configuration similar to that of the first embodiment, and can inject a medical solution by performing a process procedure similar to that shown in FIG. 5.

The capsule inserting system according to the second embodiment uses a capsule endoscope 210 that includes a permanent magnet 218 with a magnetization direction being approximately parallel to a radial direction of a casing of the capsule endoscope, as shown in FIG. 16. Because the radial direction of the capsule endoscope 210 and the magnetization direction of the permanent magnet 218 in the capsule endoscope 210 are the same, the radial direction of the capsule endoscope 210 can be changed to a direction of a magnetic field applied. Accordingly, when a rotating magnetic field is applied to the capsule endoscope 210, the capsule endoscope 210 also rotates in accordance with rotation of the rotating magnetic field.

A distal end direction of the needle 16 is approximately parallel to the radial direction, and the needle 16 is protruded or retracted in the radial direction of the capsule endoscope 210 in accordance with driving of the actuator 15. Therefore, the magnetization direction of the permanent magnet 218 and the distal end direction of the needle 16 are approximately parallel to each other. Because the distal end direction of the needle 16 and the magnetization direction are approximately parallel, the needle 16 can puncture in a direction of the applied magnetic field and therefore the puncture direction can be uniquely determined. The needle 16 is provided with the distal end direction of the needle 16 approximately in parallel to a plane perpendicular to a long axis of the casing of the capsule endoscope 210.

Figure 17:
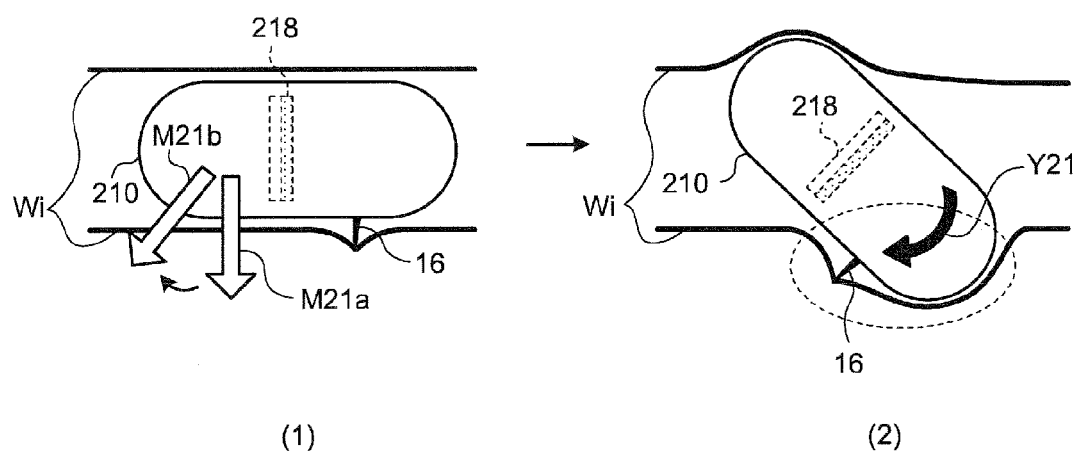
FIG. 17 is an explanatory diagram of an orientation changing process for the capsule endoscope shown in FIG. 16.

A capsule-orientation changing process during use of the capsule endoscope 210 is explained next in detail. As an example, a case that the capsule endoscope 210 is used in a narrow space as shown in FIG. 17 is explained. In this case, the magnetic field generator 2 applies a rotating magnetic field M21a to the capsule endoscope 210 to position the needle at a puncture target position within an intestine wall Wi, thereby orienting the capsule endoscope 210 in a desired posture to be taken immediately before puncture, as shown in FIG. 17(1).

Thereafter, the capsule endoscope 210 protrudes the needle 16. The magnetic field generator 2 then applies to the capsule endoscope 210, a magnetic field M21b having a direction of the magnetic field changed obliquely. That is, the magnetic field generator 2 generates a magnetic field for inclining the permanent magnet 218, thereby inclining the entire capsule endoscope 210 to orient the distal end of the protruded needle 16 toward the puncture target layer under control of the magnetic field controller 8. As a result, the orientation of the permanent magnet 218 in the capsule endoscope 210 is changed obliquely in accordance with the magnetic field direction of the magnetic field M21b, and accordingly the orientation of the entire capsule endoscope 210 is also inclined as shown by an arrow Y21 in FIG. 17(2). Tension is applied from the inclined capsule endoscope 210 to the intestine wall Wi to expand the intestine wall Wi, and elastic force (reaction force) of the intestine wall is put on the distal end of the needle 16 in contact with the expanded intestine wall Wi. This implies that large force is applied in the distal end direction of the needle 16, and accordingly the needle 16 reliably punctures the intestine wall Wi. When the needle 16 is inclined in the gravitational force direction, weights of the capsule endoscope 210 and the intestine wall can be put on the distal end of the needle 16. In the second embodiment, the needle 16 may be protruded after the capsule endoscope 210 is inclined by changing the direction of the magnetic field M21a, instead of changing the direction of the magnetic field M21a after protruding the needle 16.

Therefore, also in the second embodiment, in which the magnetization direction of the permanent magnet 218 and the distal end direction of the needle 16 are set approximately in parallel to the radial direction of the capsule endoscope, the direction of the magnetic field applied to the permanent magnet 218 is changed to provide large motion due to the change in the orientation of the entire capsule endoscope 210 to the needle 16. Accordingly, the needle 16 can be reliably stuck in the puncture target layer.

Figure 18:
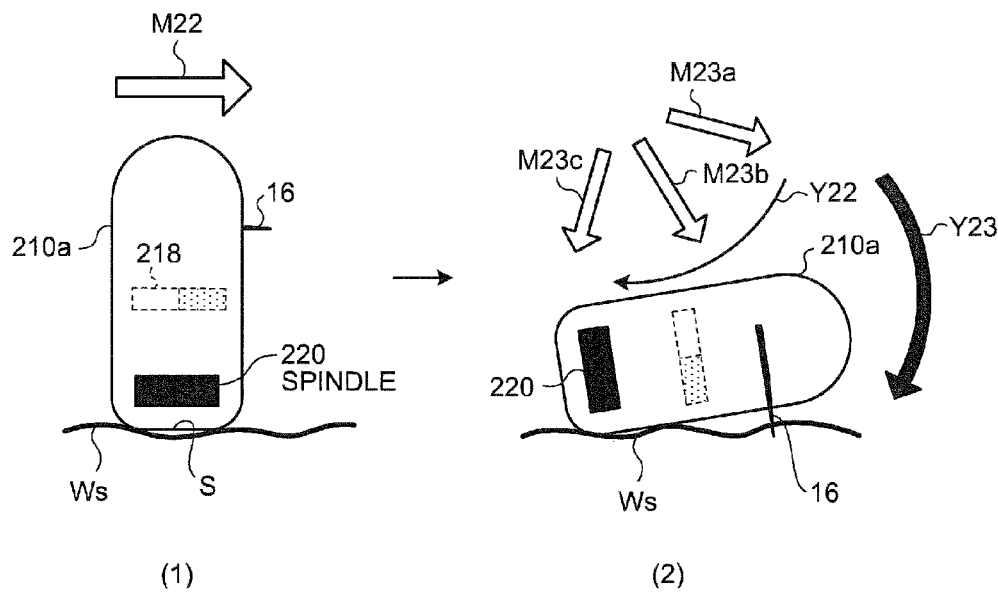
FIG. 18 is an explanatory diagram of an orientation changing process for the capsule endoscope shown in FIG. 16.

In a wide space, the magnetic field generator 2 first applies a magnetic field M22 parallel to the stomach wall Ws to a capsule endoscope 210a as shown in FIG. 18(1). In this case, with change in the orientation of the permanent magnet 218 in the capsule endoscope 210a in accordance with a magnetic field direction of the magnetic field M22, a direction of a long axis of the capsule endoscope 210a is changed to be perpendicular to the stomach wall Ws. That is, the capsule endoscope 210a assumes a posture like standing on the stomach wall Ws. The distal end of the needle 16 is protruded to be pointed in the same direction as the magnetic field M22. The magnetic field generator 2 then sequentially applies to the capsule endoscope 210a, magnetic fields M23a, M23b, and M23c with directions thereof gradually changed to follow an arrow Y22 toward the stomach wall Ws, instead of the magnetic field M22 in the same direction as the distal end direction of the protruded needle 16, as shown in FIG. 18(2). As a result, the orientation of the permanent magnet 218 is changed to follow the arrow Y22, and accordingly the capsule endoscope 210a falls down on a side in which the needle 16 is protruded as shown by an arrow Y23. A momentum caused by falling-down of the capsule endoscope 210a enables the needle 16 to be reliably stuck in the puncture target layer.

As shown in the capsule endoscope 210a, a surface S that is to be on a side facing toward the stomach wall Ws when the capsule endoscope 210a is stood (a lower surface of the capsule endoscope 210a in FIG. 18(1)) may be flattened and a weight 220 may be further provided on a side of the surface S to stand the capsule endoscope 210a on the stomach wall Ws stably in a desired posture. Instead of providing the weight 220 as shown in FIG. 18, the permanent magnet 218 may be positioned on the side of the surface S that is to be on the side facing toward the stomach wall Ws when the capsule endoscope 210a is stood, to provide a function of the weight.

In the second embodiment, magnetic attracting force can be generated when the needle is stuck in the stomach wall Ws or Wi, and the needle 16 can be stuck by applying the magnetic attracting force to the needle 16, like in the first embodiment. In this case, the magnetic field generator 2 applies a magnetic field with a magnetic flux density changed in a magnetic field direction to the capsule endoscope 210. As a result, the magnetic attracting force is generated in the magnetization direction of the permanent magnet 218 and the needle 16 can puncture due to the magnetic attracting force.

Figure 19:
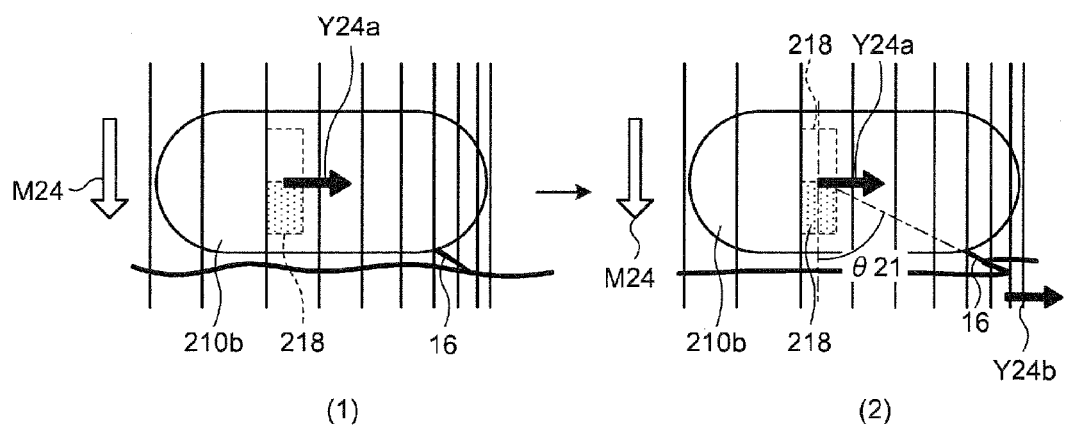
FIG. 19 is an explanatory diagram of an orientation changing process for the capsule endoscope according to the second embodiment.

The magnetic field generator 2 may apply to the capsule endoscope, a gradient magnetic field with a magnetic flux density thereof changed in a direction perpendicular to the magnetic field direction, instead of changing the magnetic flux density to the magnetic field direction. For example, a magnetic field M24 with a magnetic flux density thereof changed to a direction perpendicular to the magnetization direction of the permanent magnet 218 is applied as shown in FIG. 19(1). In this case, magnetic attracting force is generated in a direction shown by an arrow Y24a in FIG. 19(1), and a capsule endoscope 210b is moved in the direction shown by the arrow Y24a by the magnetic attracting force. Accordingly, the needle 16 protruded outside the capsule endoscope 210b is also moved in a direction shown by an arrow Y24b. In the capsule endoscope 210b, the distal end direction of the needle 16 and the magnetization direction of the permanent magnet 218 are not approximately parallel to each other to cause the needle 16 to puncture in an action like scooping. The needle 16 is provided so that the distal end direction of the needle 16 and the magnetization direction of the permanent magnet 218 form an angle $\theta 21$ equal to or larger than 45° as shown in FIG. 19(2), so that the magnetic attracting force perpendicular to the magnetization direction of the permanent magnet 218 is applied in a puncture direction of the needle 16. When the angle $\theta 21$ is equal to or larger than 45°, the magnetic attracting force in the direction shown by the arrow Y24a is applied in the puncture direction of the needle 16 as shown in FIG. 19(2). Accordingly, the needle 16 is pushed in the direction shown by the arrow Y24b against the stomach wall Ws and reliably stuck. When the angle $\theta 21$ is equal to or larger than 60°, 80% or more of components of the magnetic attracting force can be applied in the puncture direction of the needle 16. Therefore, it is desirable that the angle $\theta 21$ be equal to or larger than 60°.

Figure 20:
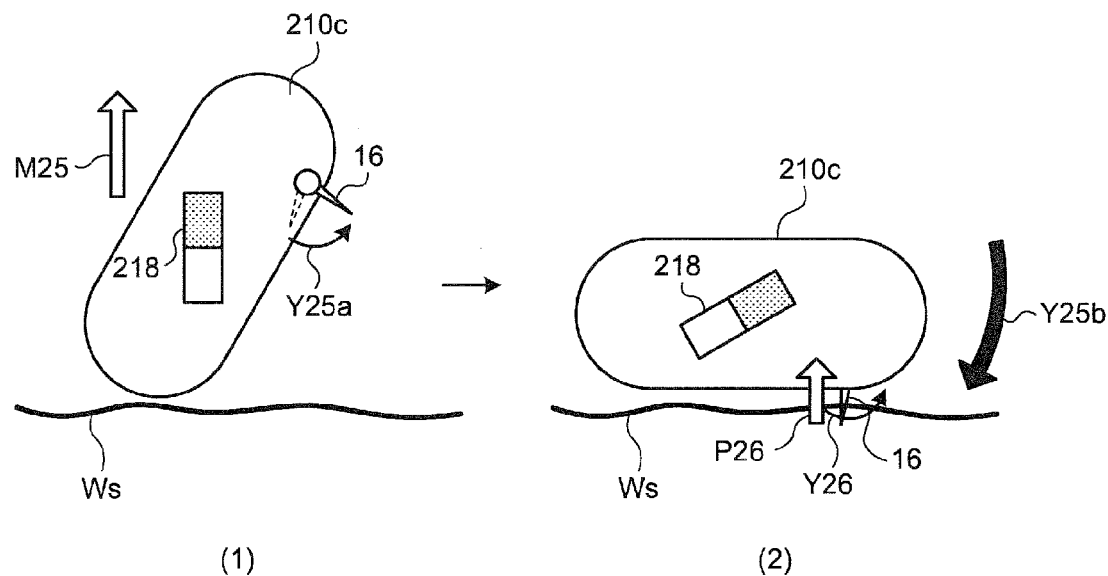
FIG. 20 is an explanatory diagram of an orientation changing process for the capsule endoscope according to the second embodiment.

Similarly to the capsule endoscope 10a shown in FIG. 8, the needle 16 may be provided such that the distal end direction of the needle 16 when protruded and a direction in which the needle 16 is protruded or retracted are differentiated as shown by an arrow Y25a in a capsule endoscope 210c shown in FIG. 20(1). As shown in FIG. 20(2), when the capsule endoscope 210c falls down and the needle 16 punctures the stomach wall Ws, reaction force P26 from the stomach wall Ws is applied to the capsule endoscope 210c in a direction different from the retraction direction of the needle 16 shown by an arrow Y26. Therefore, the needle 16 is not pushed back into the capsule endoscope 210c.

The permanent magnet 218 may be provided to be inclined with respect to a radial direction of the capsule endoscope 210c as shown in FIG. 20(1). In this case, when a magnetic field M25 in a vertical direction is applied, the orientation of the permanent magnet 218 is changed in the same direction as the magnetic field M25, and accordingly the body of the capsule endoscope 210c stands to be inclined with respect to the stomach wall Ws. The needle 16 is provided to be protruded from an inclined surface of the capsule endoscope 210c on a side of the stomach wall Ws when the body of the capsule endoscope 210c stands up from the stomach wall Ws. In this way, when the magnetic field M25 is applied, the capsule endoscope 210c can be positioned to reliably orient the distal end of the needle 16 toward the stomach wall Ws. When application of the magnetic field M25 is stopped, the capsule endoscope 210c falls down as shown by an arrow Y25b with the needle 16 pointing downward due to a weight of the inclined capsule endoscope 210c. Accordingly, the needle 16 can be reliably stuck in the stomach wall Ws.

Third Embodiment

Figure 21:
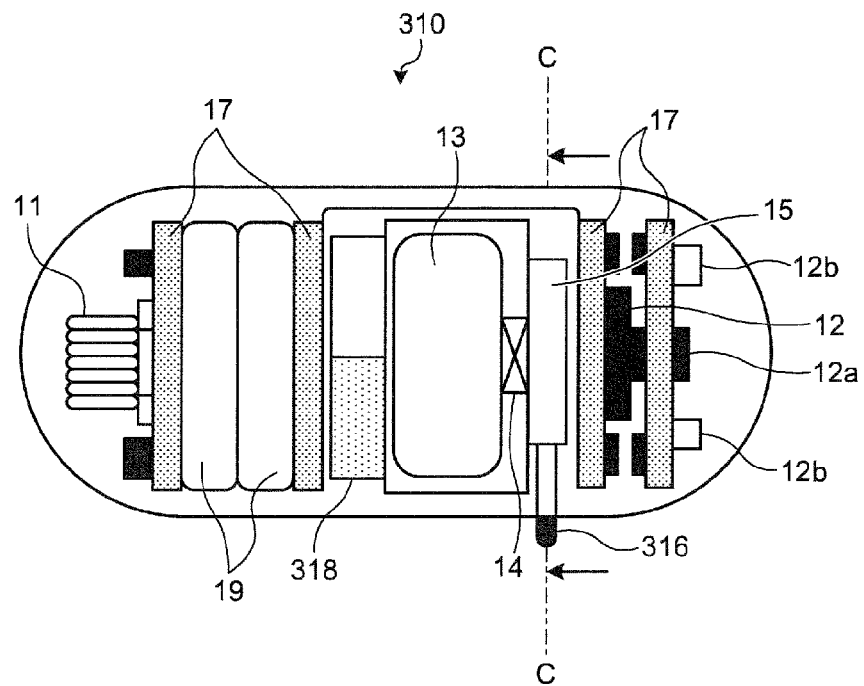
FIG. 21 is a schematic diagram of an internal configuration of a capsule endoscope according to a third embodiment.
Figure 22:
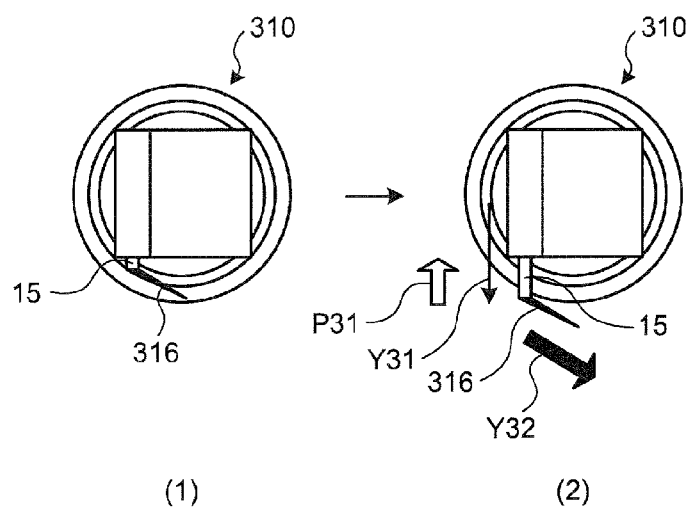
FIG. 22 is a cross-sectional view along a line C-C in FIG. 21.

A third embodiment is explained next. FIG. 21 depicts an internal configuration of a capsule endoscope according to the third embodiment. FIG. 22 is a cross-sectional view along a line C-C in FIG. 21. A capsule inserting system according to the third embodiment has a configuration similar to that shown in FIG. 1, and can inject a medical solution by performing a process procedure similar to that shown in FIG. 5.

The capsule inserting system according to the third embodiment uses a capsule endoscope 310 including a permanent magnet 318 with a magnetization direction approximately parallel to a radial direction of a casing as shown in FIG. 21, similarly to the capsule endoscope 210.

As shown in FIGS. 21 and 22, the actuator 15 is connected to a rear end of a needle 316 to form an angle equal to or larger than 90° and equal to or smaller than 135°. Thus, when the actuator 15 is moved toward an outer circumferential side of the capsule endoscope 310 as shown by an arrow Y31 in FIG. 22(2), the needle 316 is protruded from an outer surface of the capsule endoscope 310 as shown by an arrow Y32. Therefore, because the distal end direction of the needle 316 when protruded and a direction of protrusion or retraction of the needle 316 are different from each other, the protruded needle 316 is not pushed back into the capsule endoscope 310 even when reaction force P31 is applied from an intestine wall or the like due to motion of the capsule endoscope 310 in a direction shown by the arrow Y31.

Figure 23:
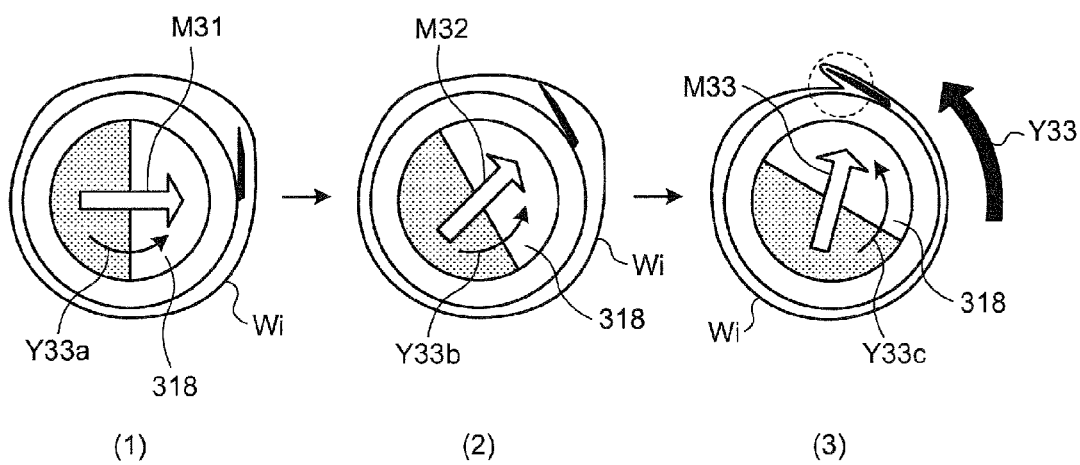
FIG. 23 is an explanatory diagram of an orientation changing process for the capsule endoscope shown in FIGS. 21 and 22.

In the capsule endoscope 310, the radial direction of the capsule endoscope 310 and the magnetization direction of the permanent magnet 318 in the capsule endoscope 310 are the same. Therefore, the radial direction of the capsule endoscope 310 can be changed to a direction of a magnetic field applied. Specifically, when a rotating magnetic field around a lumen like magnetic fields M31 to M33 shown in FIGS. 23(1) to 23(3) is applied, the permanent magnet 318 is also rotated around a long axis of the capsule endoscope 310 with rotation of the rotating magnetic field as shown by arrows Y33a, Y33b, and Y33c. Accordingly, the entire capsule endoscope 310 is also rotated as shown by an arrow Y33. In this case, the protruded needle 316 is also moved with rotation of the entire capsule endoscope 310, and accordingly an intestine wall Wi caught in the distal end of the needle 316 is expanded as shown in FIG. 23(3). Therefore, a momentum produced by the rotation of the entire capsule endoscope 310 is applied to the distal end of the needle 316, so that the needle 316 is reliably stuck in the intestine wall Wi.

Figure 24:
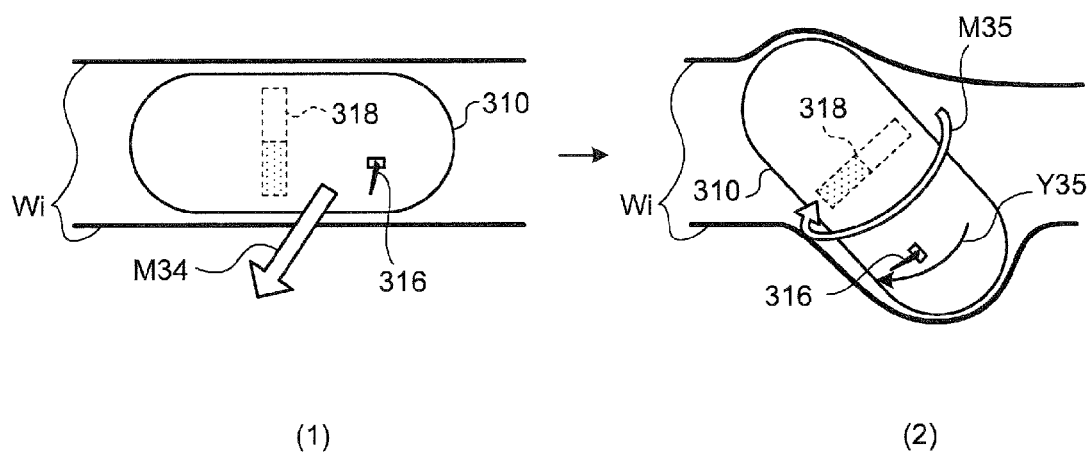
FIG. 24 is an explanatory diagram of an orientation changing process for the capsule endoscope shown in FIGS. 21 and 22.

The magnetic field generator 2 may apply a magnetic field M34 that is oblique with respect to a lumen as shown in FIG. 24(1) to incline the capsule endoscope 310, thereby expanding the intestine wall Wi as shown in FIG. 24(2), and then apply a rotating magnetic field M35 that has the same angle as that of the magnetic field M34 and rotates along an outer circumference of the capsule endoscope 310. The capsule endoscope 310 is also rotated as shown by an arrow Y35 with rotation of the rotating magnetic field M35. Therefore, the needle 316 protruded from an outer surface of the capsule endoscope 310 is reliably stuck in the expanded intestine wall Wi.

As described above, also when the needle 316 is protruded from the outer surface of the capsule endoscope 310 like in the third embodiment, large motion produced by change in the orientation of the entire capsule endoscope 310 can be applied to the needle 316 by changing the direction of the magnetic field applied to the permanent magnet 318. Thus, the needle 316 can be reliably stuck in the puncture target layer.

Figure 25:
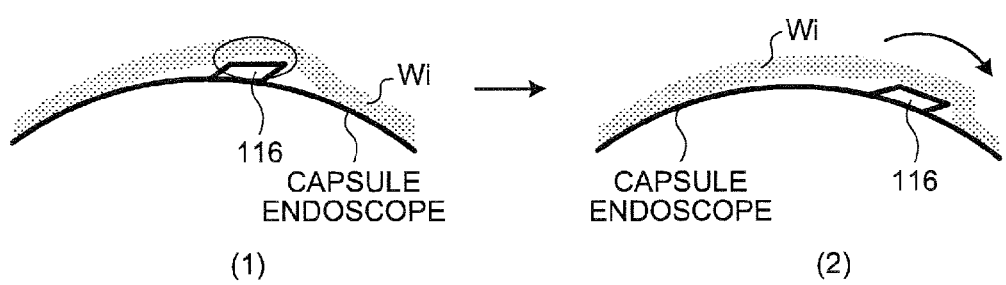
FIG. 25 is an explanatory diagram of a needle included in the capsule endoscope according to the conventional technique.

The capsule endoscope 310 is rotated by the rotating magnetic field after the distal end of the needle 316 catches a tissue of the puncture target layer such as the intestine wall to cause the needle 316 to reliably puncture. However, when a needle protrusion length is too short and the distal end of the needle 116 does not catch a tissue of the puncture target layer such as the intestine wall Wi as shown in FIG. 25(1), the distal end of the needle 116 slips on a surface of the tissue of the intestine wall Wi and is idly turned as shown in FIG. 25(2), and thus the needle 116 is not stuck, even when the entire capsule endoscope is rotated. Accordingly, it is necessary to set the protrusion length of the needle 316 or an arrangement position of the needle 316 so as to cause the distal end of the needle 316 to catch the tissue of the puncture target layer.

Figure 26:
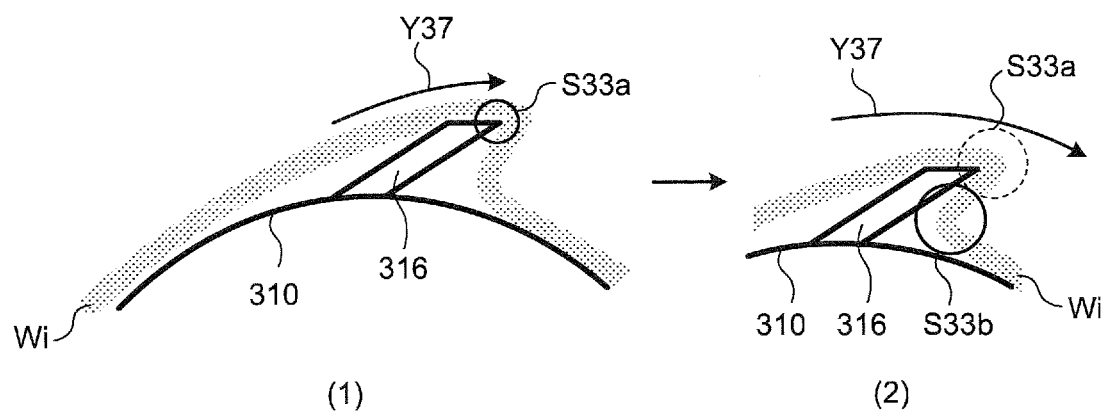
FIG. 26 is an explanatory diagram of a needle shown in FIGS. 21 and 22.

Specifically, to cause the distal end of the needle 316 to catch the intestine wall Wi in a region S33a and to expand the intestine wall Wi with rotation of the capsule endoscope 310 as shown by an arrow Y37 in FIG. 26(1), a space sufficient for the tissue of the intestine wall Wi to enter between the distal end of the needle 316 and the casing of the capsule endoscope 310 as shown by a region S33b in FIG. 26(2) is required.

Figure 27:
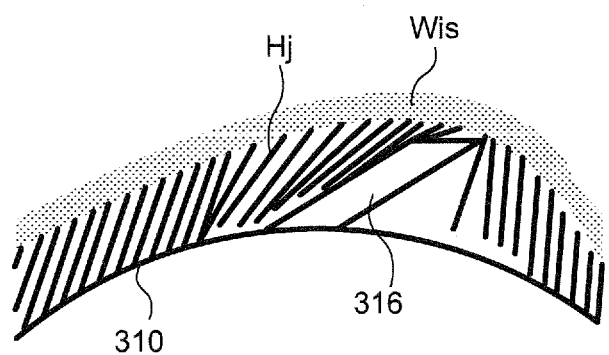
FIG. 27 is an explanatory diagram of the needle shown in FIGS. 21 and 22.
Figure 28:
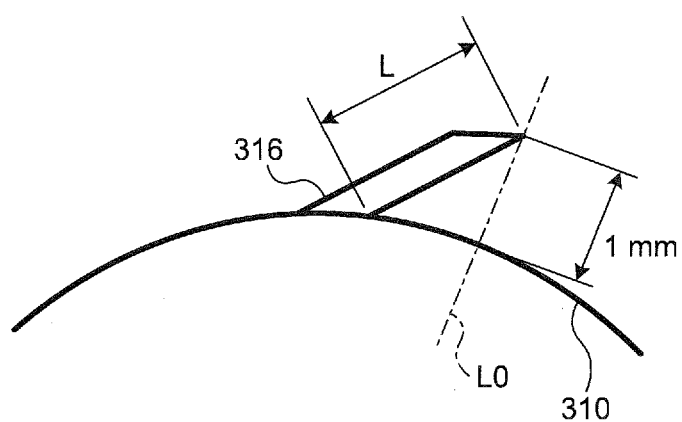
FIG. 28 is an explanatory diagram of the needle shown in FIGS. 21 and 22.

A specific structure of the needle 316 and installation position conditions therefor are explained in more detail assuming an example where a human small intestine is a puncture target layer for the needle. As shown in FIG. 27, a mucosal layer Wis of the small intestine is made of tissues called villi Hj in the form of capillary hairs extending toward an inner cavity. Lengths of the villi Hj are about 1 millimeter. A submucosal layer to which the medical solution is to be injected is at roots of the villi Hj. Accordingly, when the structure and installation position of the needle 316 is set to form a space beyond 1 millimeter between the distal end of the needle 316 and the casing of the capsule endoscope 310 on a straight line L0 connecting the distal end of the needle 316 and a center of an outer circumference of the capsule endoscope 310 as shown in FIG. 28, the villi Hj enter the space and the distal end of the needle 316 can reach the target submucosal layer. When the entire capsule endoscope 310 is rotated around the long axis of the capsule endoscope 310 with the distal end of the needle 316 reaching the submucosal layer, the needle 316 can puncture the submucosal layer, enabling injection of the medical solution.

Figure 29:
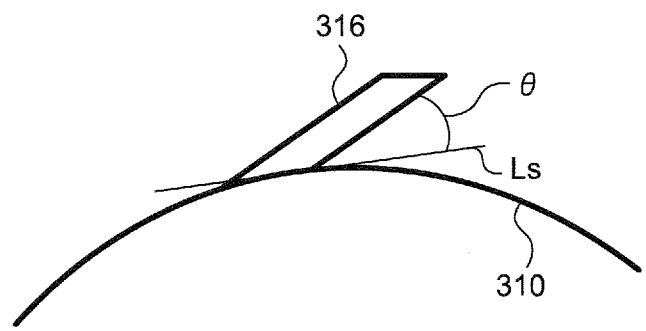
FIG. 29 is an explanatory diagram of the needle shown in FIGS. 21 and 22.
Figure 30:
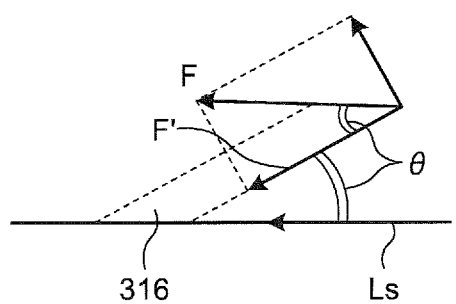
FIG. 30 is an explanatory diagram of the needle shown in FIGS. 21 and 22.

A protrusion angle of the needle 316 that provides the space beyond 1 millimeter between the distal end of the needle 316 and the casing of the capsule endoscope 310 on the straight line L0 connecting the distal end of the needle 316 and the center of the outer circumference of the capsule endoscope 310 is now explained. It is assumed that the protrusion angle of the needle 316 is an angle θ formed by a lower external tangent of the needle 316 on a side of the casing of the capsule endoscope 310 and a tangent line Ls at a point where the external tangent intersects with the outer circumference of the casing of the capsule endoscope 310 as shown in FIG. 29. When the capsule endoscope 310 is rotated around its long axis, force F from small intestine tissues is put on the distal end of the needle 316 in a direction approximately parallel to the tangent line Ls as shown in FIG. 30. A component of the force F parallel to a moving direction of the needle 316 is puncture force F' of the needle 316 onto the small intestine tissues. Because the protrusion angle of the needle 316 is the angle θ formed by the external tangent and the tangent line Ls, the puncture force F' has a magnitude of F cos θ. When the angle θ is equal to or smaller than 45°, the puncture force F' is larger than a component of the force F perpendicular to the puncture force F'. Therefore, force generated by rotation of the capsule endoscope 310 can be efficiently used for puncture. Accordingly, it is desirable that the protrusion angle θ of the needle 316 be equal to or smaller than 45°.

Figure 31:
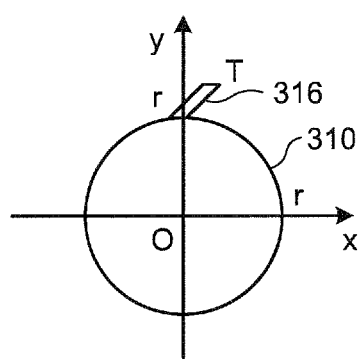
FIG. 31 is an explanatory diagram of the needle shown in FIGS. 21 and 22.

A minimum value of a protrusion length L of the needle 316 is explained. A cross section of the capsule endoscope 310 including the needle 316 perpendicular to the long axis direction of the capsule endoscope is obtained, and a coordinate system is applied thereto with the long axis of the capsule endoscope 310 as an origin as shown in FIG. 31. An outside diameter of the capsule endoscope 310 is denoted by 2r and a point corresponding to the distal end of the needle 316 is denoted by T.

Figure 32:
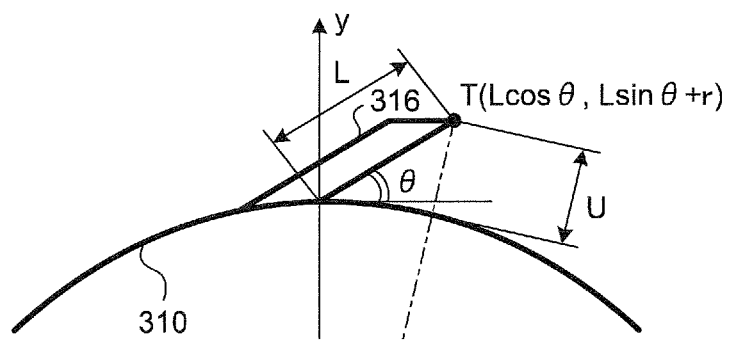
FIG. 32 is an explanatory diagram of the needle shown in FIGS. 21 and 22.

As shown in FIG. 32, when the protrusion angle of the needle 316 is θ and the protrusion length of the needle 316 is L, the point T has coordinates of (L cos θ, L sin θ+r). In this example, an under needle length U between the distal end of the needle 316 and the casing of the capsule endoscope 310 is given by an Expression (1).

$$U=((L\cos\theta)^2+(L\sin\theta+r)^2)^{1/2}-r \quad (1)$$

As described above, it is necessary that the under needle length U be equal to or larger than 1 millimeter, and thus $U \geq 1$ holds true. Accordingly, an Expression (2) is derived from the Expression (1).

$$L^2+2rL\sin\theta-(2r+1)\geq 0 \quad (2)$$

As can be seen from FIG. 32, when the protrusion length L is fixed, the under needle length U is increased when the protrusion angle θ is increased. In other words, a value of the length L satisfying $U \geq 1$ is smaller when the protrusion angle θ is larger. Because the protrusion angle θ is desirably equal to or smaller than 45°, the protrusion length L has a minimum value when the protrusion angle θ is 45°. When θ=45° is assigned to the Expression (2), an Expression (3) is obtained.

$$L^2+2^{1/2}rL-(2r+1)\geq 0 \quad (3)$$

When the Expression (3) is transformed, an Expression (4) is obtained.

$$(L+2^{1/2}r/2)^2(r^2/2+2r+1)\geq 0 \quad (4)$$

When assuming $X=L+2^{1/2}r/2$ and $P=r^2/2+2r+1$ in the Expression (4), an Expression (5) is obtained.

$$X^2-P=(X+P^{1/2})(X-P^{1/2})\geq 0 \quad (5)$$

Because r>0, P>0 is derived.

Therefore, $P^{1/2}>0$ holds true, and therefore a range of X satisfying the Expression (5) is $P^{1/2} \leq X$. When $X=L+2^{1/2}r/2$ and $P=r^2/2+2r+1$ are assigned thereto, an Expression (6) is obtained.

$$L+2^{1/2}r/2\geq(r^2/2+2r+1)^{1/2} \quad (6)$$

From the Expression (6), $L_{min}$ as a minimum value of L is given by an Expression (7).

$$L_{min}=(r^2/2+2r+1)^{1/2}-2^{1/2}r/2 \quad (7)$$

When a value of r is smaller, the minimum value $L_{min}$ of L satisfying $U \geq 1$ is smaller.

The capsule endoscope 310 for small intestine usually has an outside diameter equal to or larger than 5 millimeters. Therefore, assuming $R \geq 5$, a minimum value of r is 2.5 millimeters. By assigning 2.5 millimeters as the minimum value of r to the Expression (7), the value $L_{min}$ can be given by an Expression (8).

$$L \approx 1.253 \text{ [mm]} \quad (8)$$

As described above, the minimum value of the protrusion length L of the needle 316 is 1.253 millimeters. Therefore, when the protrusion length L is longer than 1.26 millimeters, the space with a height above the length of the villi Hj of 1 millimeter can be formed between the needle 316 and the casing of the capsule endoscope 310.

A maximum diameter of the capsule endoscope 310 is desirably equal to or smaller than 20 millimeters in view of insertability into a subject. When the diameter of the casing of the capsule endoscope 310 is smaller, the height of the space formed between the needle 316 and the casing exceeds 1 millimeter, and thus the protrusion length L of the needle 316 can be reduced. Therefore, the actuator 15 that drives protrusion or retraction of the needle 316 can be further downsized.

First Modification

Figure 33:
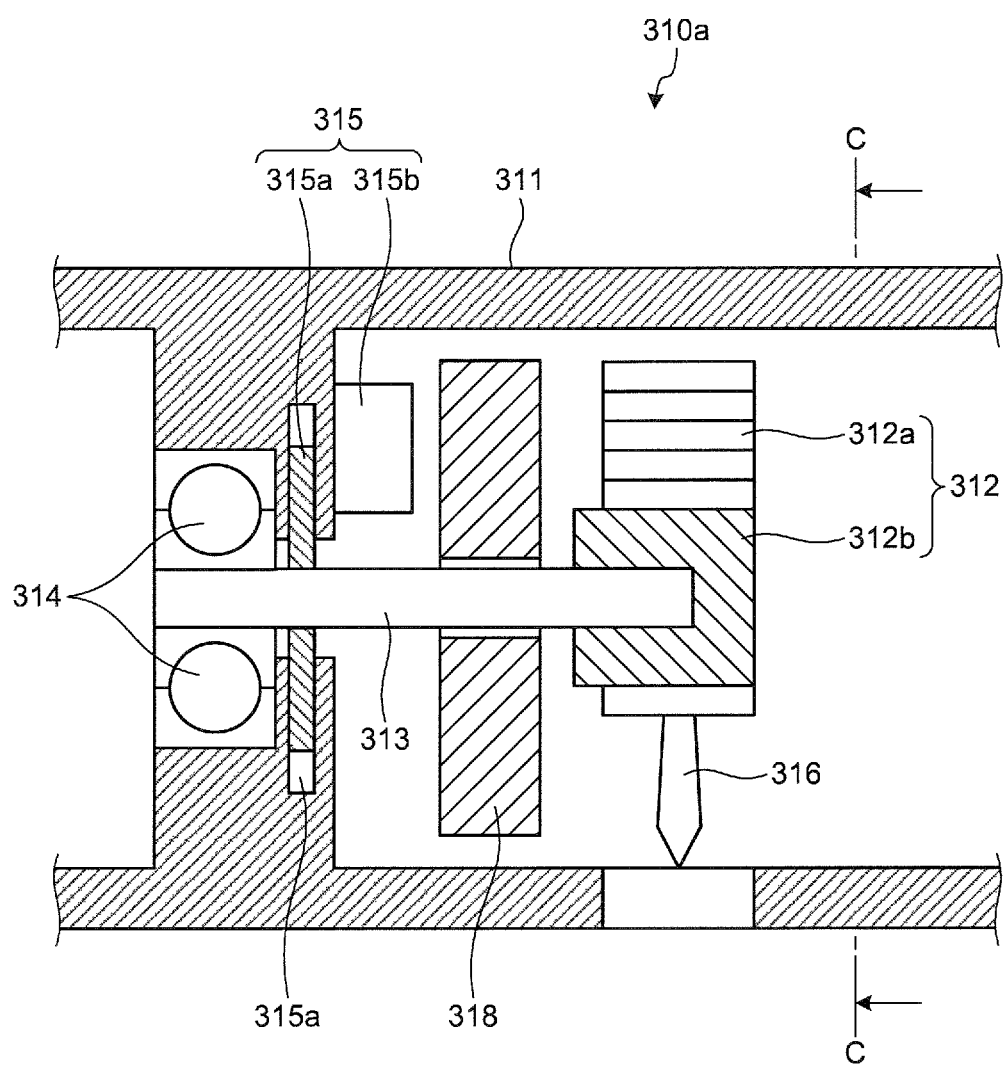
FIG. 33 is a schematic diagram of a configuration example of a capsule endoscope according to a first modification of the present invention.
Figure 34:
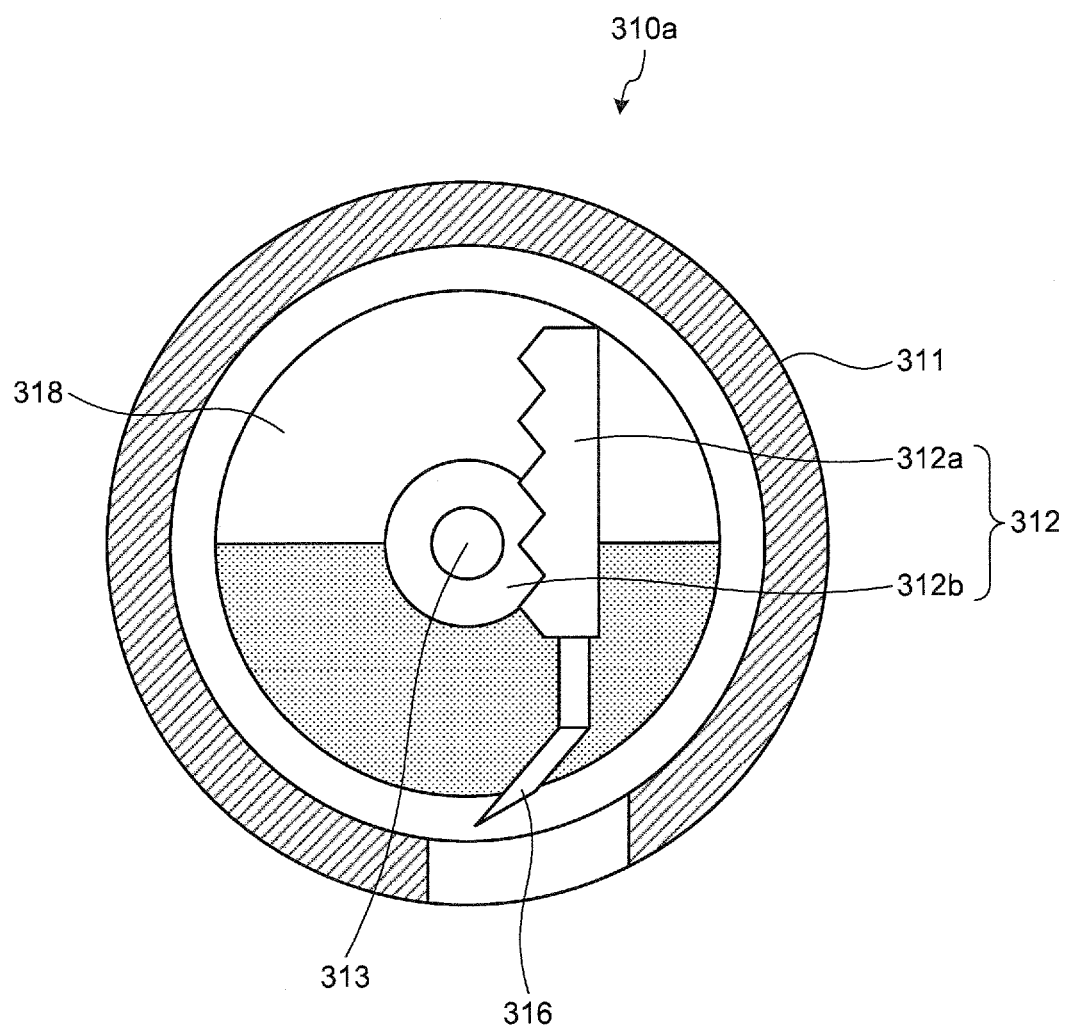
FIG. 34 is a cross-sectional view of the capsule endoscope shown in FIG. 33 along a line C-C.

A first modification of the capsule endoscope according to the present invention is explained next. In the capsule endoscope 310 according to the third embodiment described above, the needle 316 is protruded or retracted by driving the actuator 15. However, the needle 316 may be protruded or retracted by rotating the permanent magnet 318. FIG. 33 is a schematic diagram of a configuration example of a capsule endoscope according to the first modification of the present invention. FIG. 34 is a cross-sectional view of the capsule endoscope shown in FIG. 33 along a line C-C. FIG. 34 depicts a protruding and retracting mechanism unit for the needle 316, which is a relevant part of a capsule endoscope 310a according to the first modification.

As shown in FIGS. 33 and 34, the capsule endoscope 310a according to the first modification includes, within a capsule-shaped casing 311 having a structure similar to that of the capsule endoscope 310 according to the third embodiment described above, a protruding and retracting mechanism 312 that protrudes or retracts the needle 316 by rotational force of the permanent magnet 318, a rotation axis 313 that supports the protruding and retracting mechanism 312 and the permanent magnet 318, a bearing 314 that rotatably supports the rotation axis 313, and a connection-state switching unit 315 that switches a connection state of the permanent magnet 318 to the casing 311. Although not shown, the needle 316 is communicated with the valve 14 through a tube or the like. The remaining parts of the configuration of the first modification other than these components are the same as those of the third embodiment, and like parts are denoted by like reference letters or numerals.

The protruding and retracting mechanism 312 protrudes or retracts the needle 316 from or into the casing 311 with relative rotation of the permanent magnet 318 to the casing 311. As shown in FIGS. 33 and 34, the protruding and retracting mechanism 312 is realized by combining a rack 312a and a pinion gear 312b engaging with each other. The rack 312a is a rod-like member including teeth engaged with the pinion gear 312b. The needle 316 inclined in the same manner as in the third embodiment described above is fixed to an end of the rack 312a. In this case, the needle 316 is provided to have a distal end direction in plane with the magnetization direction of the permanent magnet 318. The rack 312a transforms rotational motion of the pinion gear 312b to linear motion, thereby protruding the needle 316 from the casing 311 or retracting the protruded needle 316 into the casing 311. The pinion gear 312b is fixed to an end of the rotation axis 313 and positioned to engage with the rack 312a. The pinion gear 312b transmits rotational motion of the permanent magnet 318 to the rack 312a via the rotation axis 313.

The rotation axis 313 is fixed to the permanent magnet 318, being inserted into a through hole formed at an approximate center of the permanent magnet 318 as shown in FIG. 33. The pinion gear 312b is attached to one end of the rotation axis 313 as described above, and the other end of the rotation axis 313 is attached to the bearing 314. The bearing 314 is positioned at an extending portion on an internal wall side of the casing 311 and rotatably supports the other end of the rotation axis 313 as shown in FIG. 33.

The connection-state switching unit 315 switches the connection state of the permanent magnet 318 to the casing 311, and is realized by a movable connecting member 315a and an actuator 315b as a driving source for the connecting member 315a. The connecting member 315a is positioned at the extending portion on the inner wall side of the casing 311 as shown in FIG. 33. The connecting member 315a connects the permanent magnet 318 to the casing 311 via the rotation axis 313, thereby switching the connection state of the permanent magnet 318 to the casing 311 between a fixed state and a movable state. Specifically, the connecting member 315a is moved toward the rotation axis 313 by driving force of the actuator 315b, thereby laterally sandwiching the rotation axis 313 (see FIG. 33). As a result, the connecting member 315a puts the permanent magnet 318 in a fixed state with respect to the casing 311 through the rotation axis 313. The connecting member 315a is also moved away from the rotation axis 313 by the driving force of the actuator 315b to cancel the sandwich state of the rotation axis 313. As a result, the connecting member 315a cancels the fixed state of the permanent magnet 318 with respect to the casing 311, thereby putting the permanent magnet 318 in the movable state with respect to the casing 311. The actuator 315b is driven and controlled by the control circuit on the control board 17.

Figure 35:
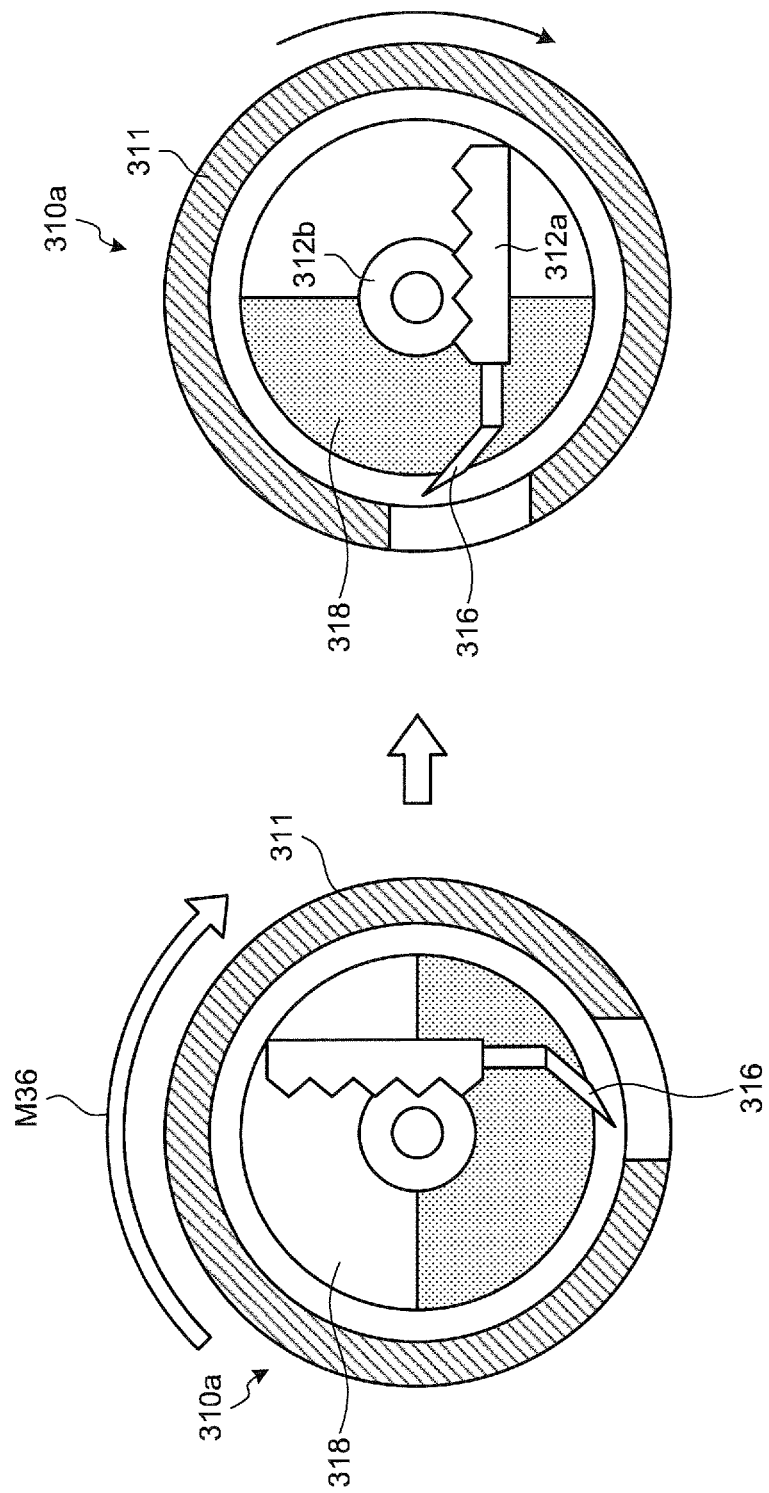
FIG. 35 is a schematic diagram exemplifying an operation of a capsule endoscope when a connection state of a permanent magnet with respect to a casing is a fixed state.

The fixed state of the permanent magnet 318 with respect to the casing 311 is a state in which the permanent magnet 318 is fixed relative to the casing 311 through the rotation axis 313. FIG. 35 is a schematic diagram exemplifying an operation of the capsule endoscope when the connection state of the permanent magnet with respect to the casing is the fixed state. The permanent magnet 318 in the fixed state with respect to the casing 311 is rotated with the casing 311 following a magnetic field M36 externally applied, as shown in FIG. 35. The capsule endoscope 310a is rotated in a circumferential direction of the casing 311, for example, following rotation of the permanent magnet 318 in the fixed state with respect to the casing 311. In this case, because the permanent magnet 318 is not rotated relative to the casing 311, the rack 312a and the pinion gear 312b are not operated. As a result, the capsule endoscope 310a does not protrude or retract the needle 316 from or into the casing 311.

Figure 36:
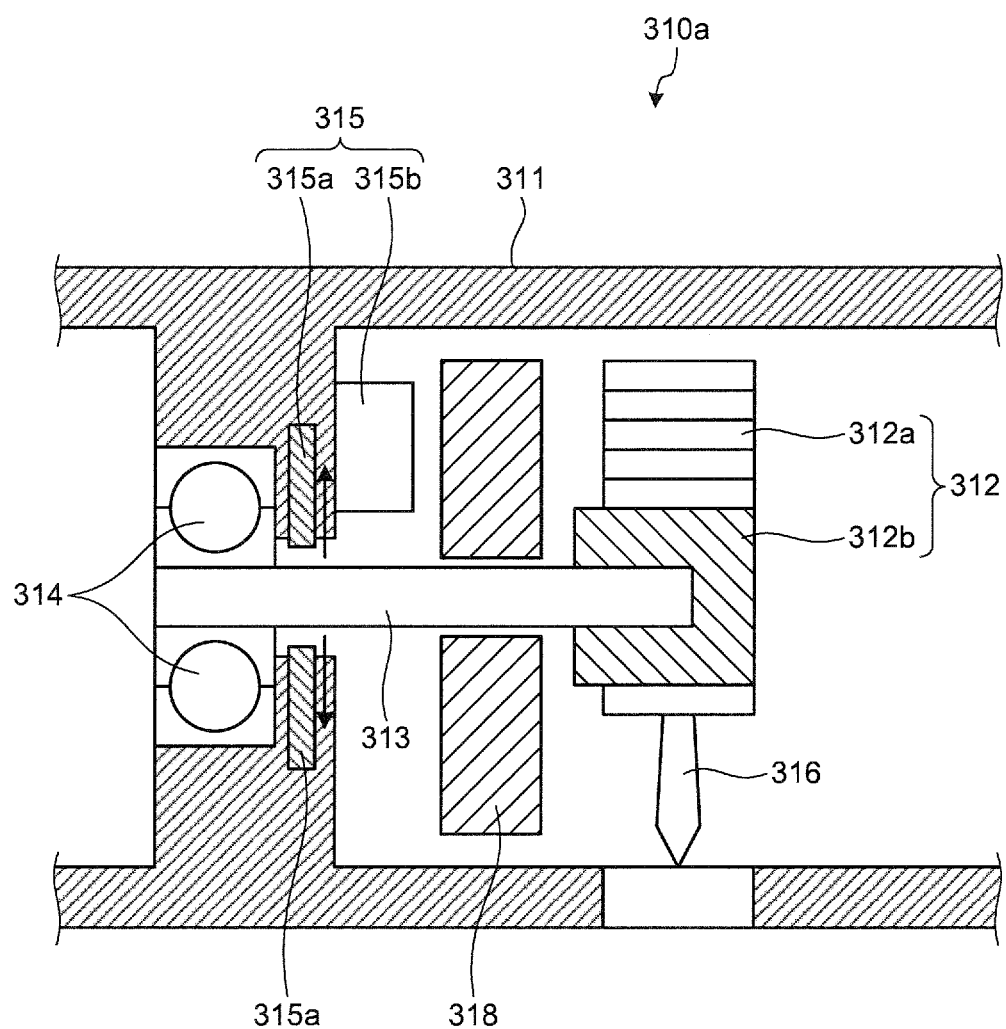
FIG. 36 is a schematic diagram of a state in which the connection state of the permanent magnet with respect to the casing is switched to a movable state by a connecting member.
Figure 37:
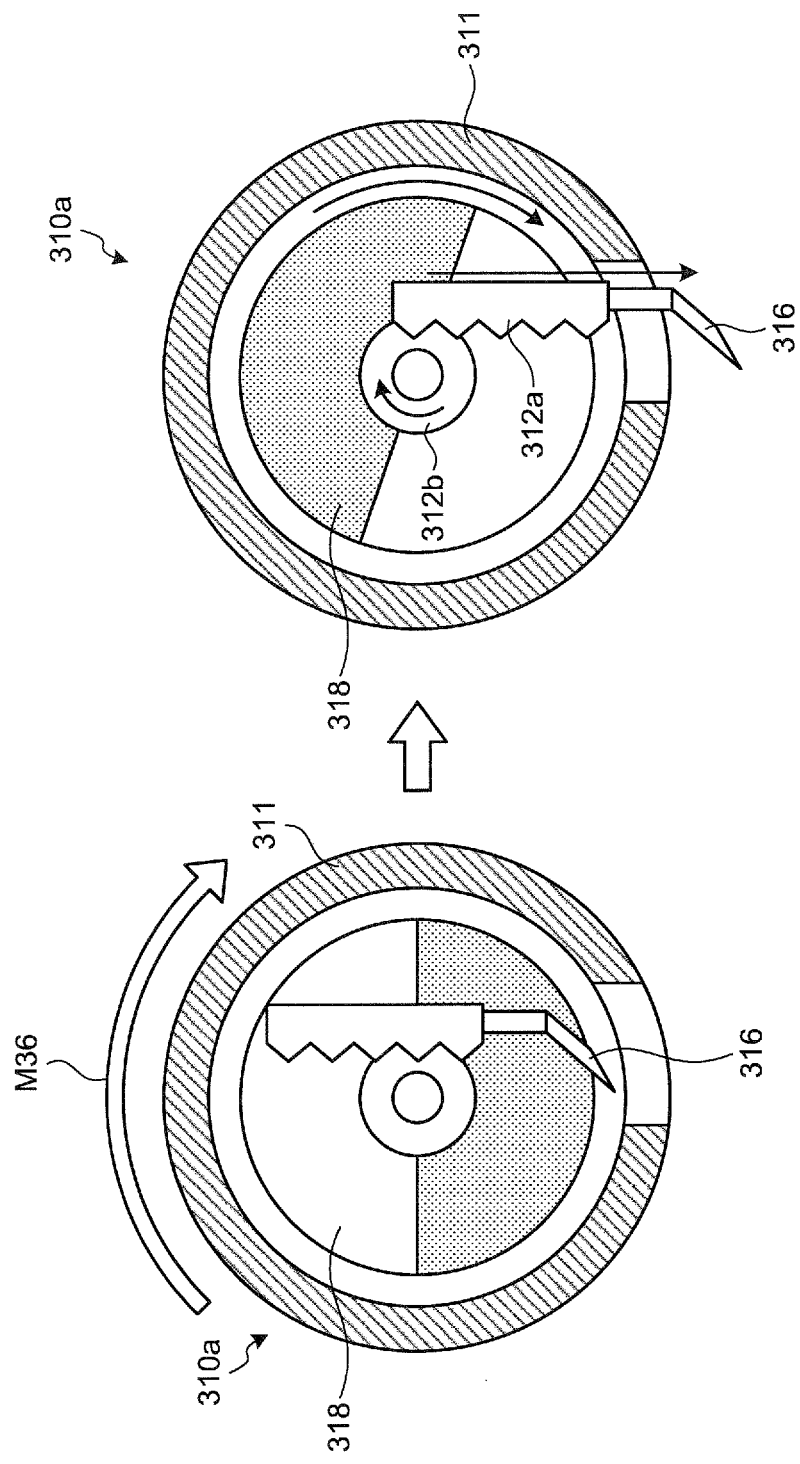
FIG. 37 is a schematic diagram exemplifying an operation of the capsule endoscope when the connection state of the permanent magnet with respect to the casing is the movable state.

In contrast, the movable state of the permanent magnet 318 with respect to the casing 311 is a state in which the permanent magnet 318 can be freely rotated relative to the casing 311. FIG. 36 is a schematic diagram of a state in which the connection state of the permanent magnet with respect to the casing is switched to the movable state by the connecting member. FIG. 37 is a schematic diagram exemplifying an operation of the capsule endoscope when the connection state of the permanent magnet with respect to the casing is the movable state. As shown in FIGS. 36 and 37, the permanent magnet 318 in the movable state with respect to the casing 311 is rotated relative to the casing following the magnetic field M36 externally applied. In this case, the permanent magnet 318 transmits the rotational motion to the pinion gear 312b through the rotation axis 313. The pinion gear 312b is rotated with the rotation of the permanent magnet 318. The rack 312a transforms the rotational motion of the pinion gear 312b to linear motion, thereby protruding the needle 316 from the casing 311 as shown in FIG. 37. When a rotating magnetic field in a direction opposite to the magnetic field M36 is applied to the permanent magnet 318 in the movable state, the permanent magnet 318 is rotated relative to the casing 311 following the opposite rotating magnetic field. In this case, the permanent magnet 318 transmits the rotational motion in the opposite direction to the pinion gear 312b through the rotation axis 313. The pinion gear 312b is rotated in the opposite direction with rotation of the permanent magnet 318. The rack 312a transforms the rotational motion of the pinion gear 312b to linear motion, thereby retracting the protruded needle 316 into the casing 311.

During the protruding or retracting operation for the needle 316, the permanent magnet 318 is in the movable state with respect to the casing 311 and therefore the capsule endoscope 310a does not rotate following the rotational motion of the permanent magnet 318 in the state.

As described above, in the first modification of the present invention, the connection state of the permanent magnet with respect to the casing can be switched by the connecting member between the fixed state and the movable state. When the connection state of the permanent magnet with respect to the casing is switched to the fixed state, the capsule endoscope is rotated following rotation of the permanent magnet in the fixed state. When the connection state of the permanent magnet with respect to the casing is switched to the movable state, the protruding and retracting mechanism for the needle is operated following rotation of the permanent magnet relative to the casing, thereby protruding or retracting the needle from or into the casing. Accordingly, magnetic guidance of the capsule endoscope and the protruding/retracting operation for the needle can be selectively performed by application of an external magnetic field. As a result, power consumption required for the magnetic guidance of the capsule endoscope and the needle protruding/retracting operation can be reduced.

The capsule endoscope 310a according to the first modification can include a helical structure on an outer surface of the casing 311 to be propelled with rotation of the permanent magnet 318 in the fixed state with respect to the casing 311. The protruding and retracting mechanism 312 for the needle 316 in the first modification may use a cam, a combination of a belt and a pulley, or a crank mechanism, instead of the combination of the rack 312a and the pinion gear 312b.

Fourth Embodiment

Figure 38:
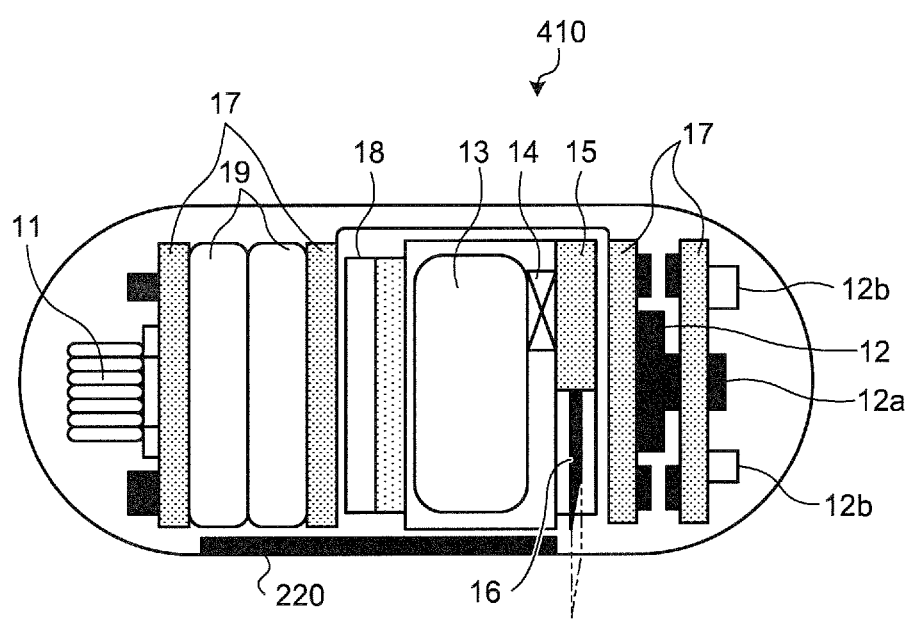
FIG. 38 is a schematic diagram of an internal configuration of a capsule endoscope according to a fourth embodiment.

A fourth embodiment is explained next. FIG. 38 depicts an internal configuration of a capsule endoscope according to the fourth embodiment. A capsule inserting system according to the fourth embodiment has a configuration similar to that shown in FIG. 1, and can inject a medical solution by performing a process procedure similar to that shown in FIG. 5.

As shown in FIG. 38, the capsule inserting system according to the fourth embodiment uses a capsule endoscope 410 including the permanent magnet 18 with a magnetization direction approximately parallel to a long axis direction of a casing of the endoscope, similarly to the capsule endoscope 10. A distal end direction of the needle 16 is approximately parallel to a radial direction, and the needle 16 is protruded or retracted in the radial direction of the capsule endoscope 410 in accordance with driving of the actuator 15. Therefore, the magnetization direction of the permanent magnet 18 and the distal end direction of the needle 16 are substantially perpendicular to each other.

Further, the weight 220 is provided in the capsule endoscope 410 on a side of the distal end of the needle 16. The weight 220 is placed at a position shifted toward the distal end of the needle 16 from a long axis of the capsule endoscope 410. This indicates that a center of gravity of the casing of the capsule endoscope 410 is shifted from the long axis of the casing of the capsule endoscope 410 due to the weight 220, and accordingly the center of gravity of the casing of the capsule endoscope 410 is located on the side of the distal end of the needle 16. In other words, the distal end direction of the needle 16 is a direction in which the gravity center of the casing of the capsule endoscope 410 shifted due to the weight 220, that is, a direction corresponding to a shifting direction of the gravity center from a central axis.

Figure 39:
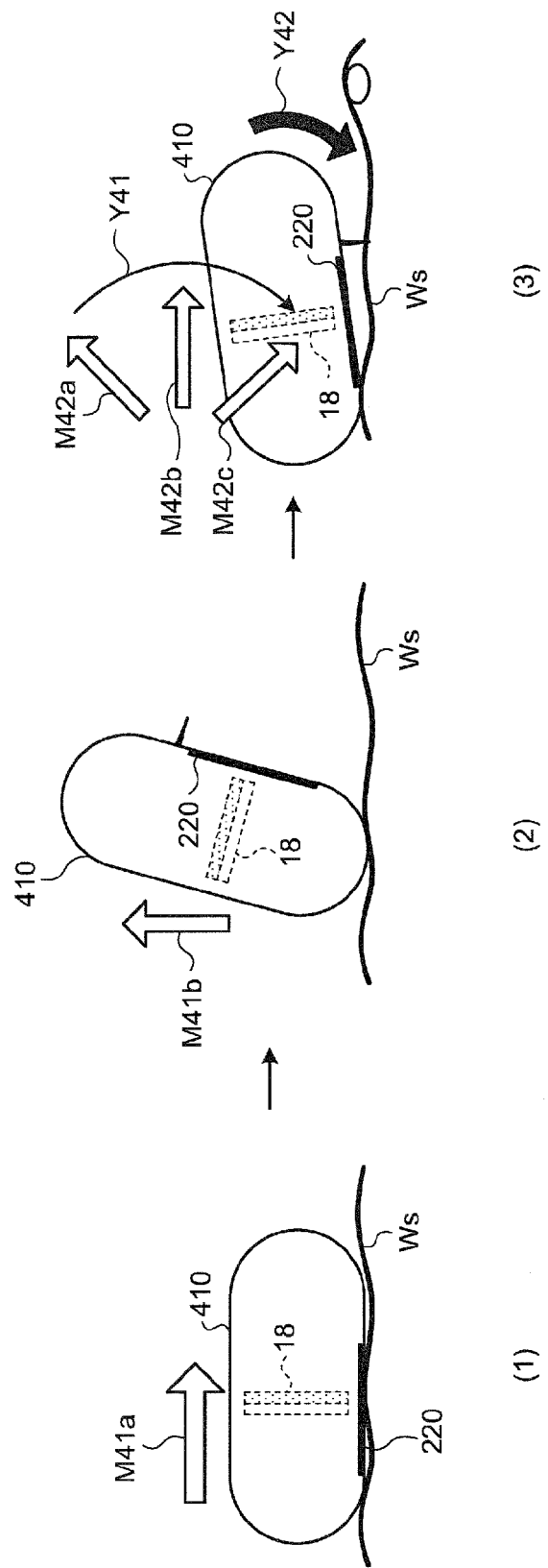
FIG. 39 is an explanatory diagram of an orientation changing process for the capsule endoscope shown in FIG. 38.

A capsule-orientation changing process performed when the capsule endoscope 410 is used is explained next in detail. As an example, a case of a wide space having a stomach wall Ws in a lower position as shown in FIG. 39 is explained. In this case, the magnetic field generator 2 applies a magnetic field M41a in a direction parallel to a surface of the stomach wall Ws to the capsule endoscope 410 as shown in FIG. 39(1). As a result, the orientation of the permanent magnet 18 is changed in accordance with the magnetic field M41a, and the orientation of the capsule endoscope 410 is changed accordingly. The capsule endoscope 410 is positioned by the weight 220 in the capsule endoscope 410 to orient the weight 220 toward the lower stomach wall Ws. The magnetic field generator 2 then applies a magnetic field M41b oriented upward of the stomach wall Ws to the capsule endoscope 410, thereby changing the orientation of the permanent magnet 18 to stand the capsule endoscope 410 up, as shown in FIG. 39(2). The magnetic field generator 2 then applies magnetic fields M42a, M42b, and M42c having directions changed from a position above the stomach wall Ws to a position near the stomach wall Ws to the capsule endoscope 410, as shown by an arrow Y41 in FIG. 39(3).

As a result, as shown by an arrow Y42, the capsule endoscope 410 falls down on the stomach wall Ws in accordance with change in the directions of the applied magnetic fields, and an entire weight of the fallen capsule endoscope 410 is put on the distal end of the needle 16. Accordingly, the protruded needle 16 is stuck in the stomach wall Ws. In this case, the capsule endoscope 410 falls down with the side on which the weight 220 is provided down. Therefore, the needle 16 provided on the side on which the weight 220 is provided reliably punctures the stomach wall Ws. Because a momentum at falling of the capsule endoscope 410 can be increased by providing the weight 220 to shift the gravity center of the capsule endoscope 410 toward the distal end of the needle from the long axis of the endoscope, puncture of the needle 16 can be made more reliable.

As described above, in the fourth embodiment, the weight 220 is provided to shift the gravity center of the capsule endoscope 410 toward the distal end of the protruded needle 16, thereby increasing reliability of the puncture of the needle 16 into the puncture target layer.

In the fourth embodiment, the magnetic field generator 2 may stop application of the magnetic field in FIG. 39(3) to zero the generated magnetic field, thereby causing the capsule endoscope 410 to fall down due to its own weight of the capsule endoscope 410. Also in this case, the capsule endoscope 410 falls down with the side on which the weight 220 is provided down, and therefore the needle 16 provided on the side of the weight 220 can reliably puncture the stomach wall Ws.

Figure 40:
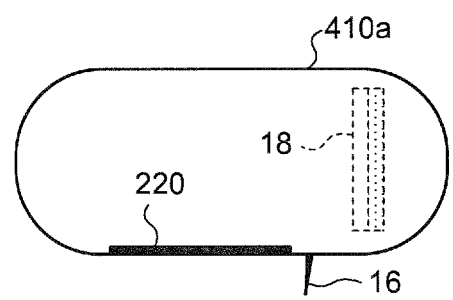
FIG. 40 is a schematic diagram of another example of the internal configuration of the capsule endoscope according to the fourth embodiment.
Figure 41:
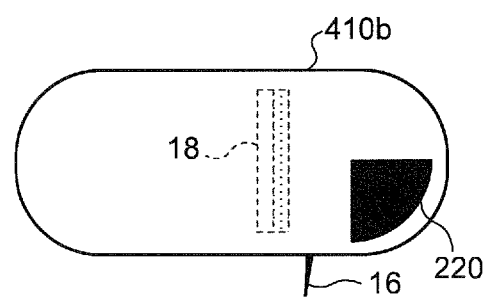
FIG. 41 is a schematic diagram of still another example of the internal configuration of the capsule endoscope according to the fourth embodiment.
Figure 42:
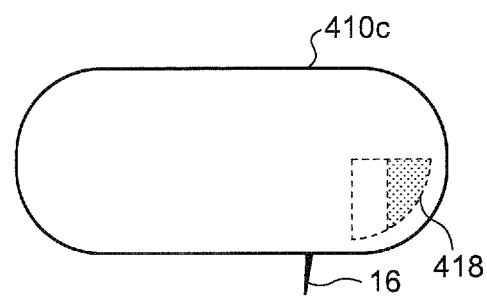
FIG. 42 is a schematic diagram of still another example of the internal configuration of the capsule endoscope according to the fourth embodiment.

In the fourth embodiment, as in a capsule endoscope 410a shown in FIG. 40, the position of the permanent magnet 18 may be shifted toward a top end of the capsule endoscope 410a. As in a capsule endoscope 410b shown in FIG. 41, the weight 220 may be shifted toward a top end of the capsule endoscope 410b. Alternatively, as in a capsule endoscope 410c shown in FIG. 42, a permanent magnet 418 may be provided in a top end direction of the capsule endoscope 410c, thereby providing a function of the weight 220. In this way, when gravity centers of the capsule endoscopes 410a, 410b, and 410c are shifted toward the distal end of the needle form the long axis of the endoscope, the standing capsule endoscope 410a can be fell down with a greater momentum, thereby making the puncture of the needle more reliable, like in the case shown in FIGS. 39(2) and 39(3).

Fifth Embodiment

Figure 43:
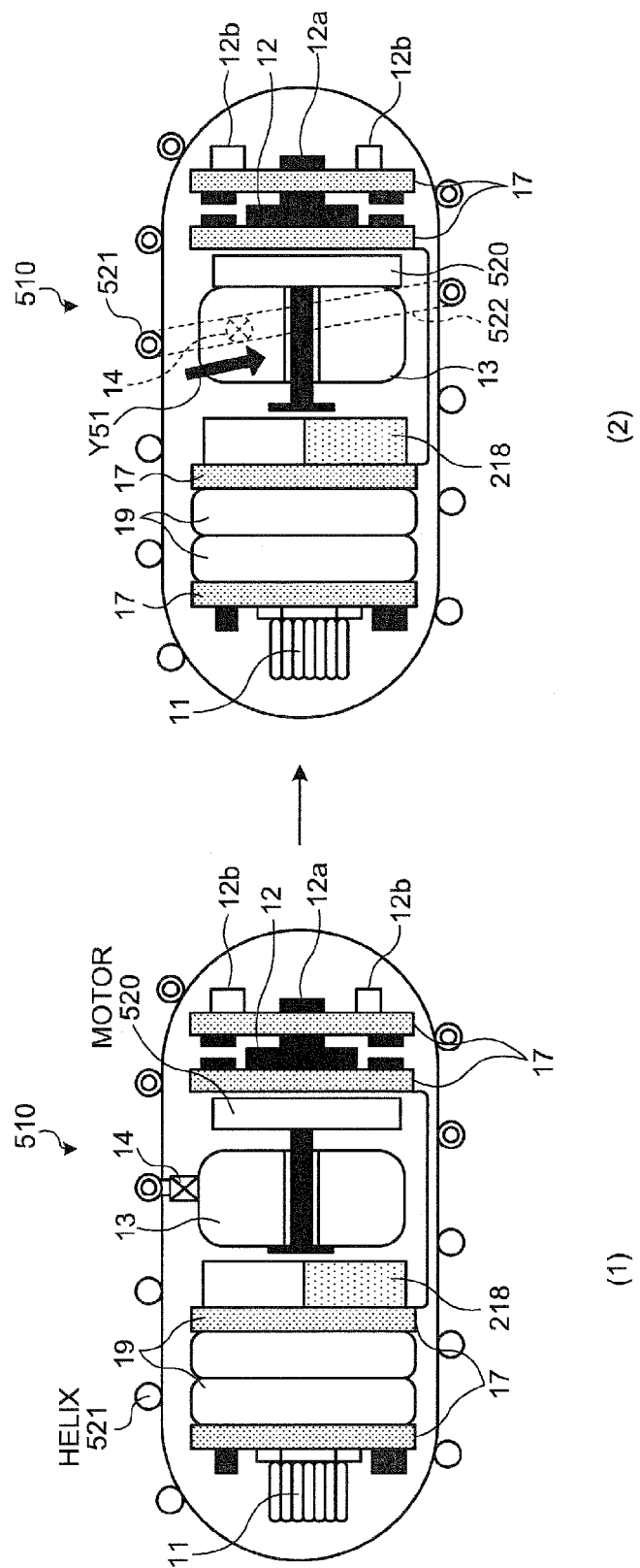
FIG. 43 is a schematic diagram of an internal configuration of a capsule endoscope according to a fifth embodiment.
Figure 44:
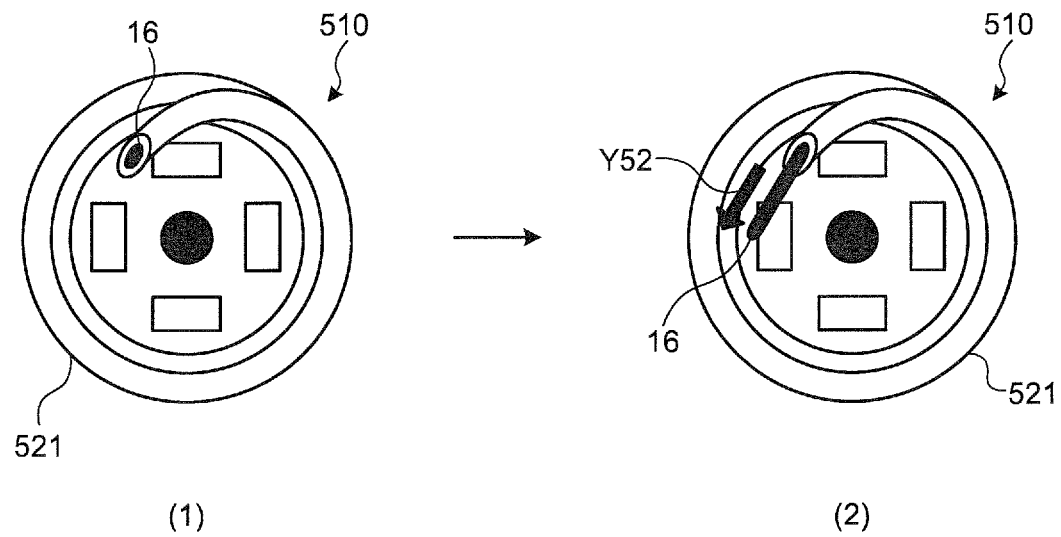
FIG. 44 is a right side view of the capsule endoscope shown in FIG. 43.

A fifth embodiment is explained next. FIG. 43 depicts an internal configuration of a capsule endoscope according to the fifth embodiment. FIG. 44 is a right side view of the capsule endoscope according to the fifth embodiment. A capsule inserting system according to the fifth embodiment has a configuration similar to that shown in FIG. 1, and can inject a medical solution by performing a process procedure similar to that shown in FIG. 5.

As shown in FIGS. 43 and 44, the capsule inserting system according to the fifth embodiment uses a capsule endoscope 510 further including a helix 521 for propelling the capsule endoscope 510 on an outer surface of a casing of the capsule endoscope, compared to the capsule endoscope 210. The helix 521 is tubular and the needle 16 is provided on a distal end of the helix 521 to be protruded as shown in FIG. 44.

The medical solution tank 13 and the valve 14 are coupled with a line formed by the helix 521 and the needle 16 provided on the distal end of the helix 521. The medical solution tank 13 and the valve 14 are integrally rotated within the casing of the capsule endoscope 510 with rotation of a motor 520. In this case, the valve 14 moves within the casing in a direction shown by an arrow Y51 in FIG. 43(2) along a channel 522 formed in the casing of the capsule endoscope 510. With rotational movement of the medical solution tank 13 and the valve 14 along the channel 522 in accordance with the rotation of the motor 520, the needle 16 coupled with the medical solution tank 13 and the valve 14 is pushed out of the helix 521 and protruded from the distal end of the helix 521 as shown by an arrow Y52 in FIG. 44(2). When the medical solution tank 13 and the valve 14 are moved up to rotatable positions, the needle 16 is completely protruded from the helix 521. When the medical solution tank 13 and the valve 14 are moved up to the rotational positions, the medical solution tank 13 and an inlet of the helix 521 in the tube are connected, so that the medical solution flows from the medical solution tank 13 into the tube of the helix 521. The motor 520 starts or stops the rotation under control of the control board 17 in accordance with an instruction of the wireless signal transmitted from the receiving unit 3. The motor 520 performs the rotational movement using the power supplied from the battery 19.

In the capsule endoscope 510, a rotating magnetic field is applied around a long axis of the capsule endoscope 510 to rotate the capsule endoscope 510. When the capsule endoscope 510 rotates, the helix 521 engages with a wall of a digestive tract in the body, so that the capsule endoscope 510 can move in an axial direction like a screw.

In the fifth embodiment, the magnetic field controller 8 causes the magnetic field generator 2 to generate a rotating magnetic field for rotating the permanent magnet 218 to match a protruding direction of the needle 16 with a propelling direction of the helix 521, thereby rotating the entire capsule endoscope 510.

Figure 45:
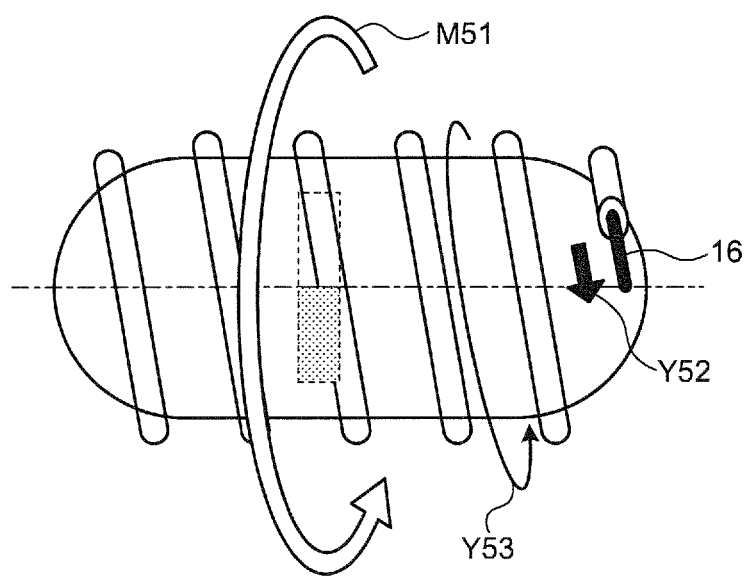
FIG. 45 is an explanatory diagram of an orientation changing process for the capsule endoscope shown in FIGS. 43 and 44.

Specifically, as shown in FIG. 45, to propel the helix 521 in a direction shown by an arrow Y53, which is the same direction as the protruding direction of the needle 16 shown by an arrow Y52, the magnetic field generator 2 applies a rotating magnetic field M51 rotating in the direction shown by the arrow Y53 to the capsule endoscope 510. As a result, the capsule endoscope 510 rotates as shown by the arrow Y53, and the helix 521 is propelled in the direction shown by the arrow Y53. Therefore, the distal end of the needle 16 protruding from the distal end of the helix 521 is also moved in the direction shown by the arrow Y53 in accordance with propulsion of the helix 521 in the direction shown by the arrow Y53. The needle 16 is then stuck in a puncture target layer (not shown) below the capsule endoscope 510. Because an entire weight of the capsule endoscope 510 rotated by the rotating magnetic field M51 is put on the distal end of the needle 16, the needle 16 is reliably stuck in the puncture target layer in accordance with great momentum produced by the entire weight of the capsule endoscope 510. The user can instruct through the input unit 6 to protrude the needle 16 by rotating the motor 520 while the capsule endoscope 510 is rotating during application of the rotating magnetic field M51. The user also can instruct through the input unit 6 to protrude the needle 16 by rotating the motor 520 when the capsule endoscope 510 is rotated by application of the rotating magnetic field M51 and the distal end of the helix 521 is brought in contact with the puncture target layer.

Also when the needle 16 is provided at the distal end of the helix 521 like in the fifth embodiment, the magnetic field controller 8 causes the magnetic field generator 2 to generate a rotating magnetic field for rotating the permanent magnet 218 to match the protruding direction of the needle 16 with the propelling direction of the helix 521, thereby providing a large motion to the needle 16. In this way, the needle 16 can be reliably stuck in the puncture target layer.

The magnetic field generator 2 may apply a gradient magnetic field to generate magnetic attracting force after applying the rotating magnetic field M51 to rotate the capsule endoscope 510, thereby improving reliability of puncture of the needle 16 of the puncture target layer.

In the first to fifth embodiments, the magnetic fields that are applied to change the orientations of the capsule endoscopes 10, 210, 310, 410, and 510 to the desired directions are explained. These magnetic fields have the directions changed in a plane approximately parallel to the distal end direction of the needle and the magnetization direction of the permanent magnet. That is, to change the distal end direction of the needle to a desired direction, the orientation of the capsule endoscope itself needs to be changed to a desired direction. Accordingly, a magnetic field in a direction that enables to change the distal end direction of the needle to the desired direction in the plane approximately parallel to the distal end direction of the needle and the magnetization direction of the permanent magnet needs to be applied to the permanent magnet. Therefore, the magnetic field controller 8 needs to cause the magnetic field generator 2 to generate a magnetic field with a direction changed in the plane approximately parallel to the distal end direction of the needle and the magnetization direction of the permanent magnet to change the orientation of the permanent magnet, thereby changing the orientation of the entire capsule endoscope.

In the first to fifth embodiments, the examples in which the receiving unit 3 transmits the wireless signal for instructing injection of the medical solution in accordance with the instruction inputted through the input unit 6 are explained. However, the present invention is not limited thereto. The receiving unit 3 may include an automatic lesion-detecting function, and may automatically transmit a wireless signal for instructing injection of the medical solution when detecting a lesion such as a bleeding site or a tumor site. In this case, the control unit 4 may operate to instruct the magnetic field controller 8 to generate a magnetic field for puncture based on a result of the lesion detection of the receiving unit 3.

Second Modification

Figure 46:
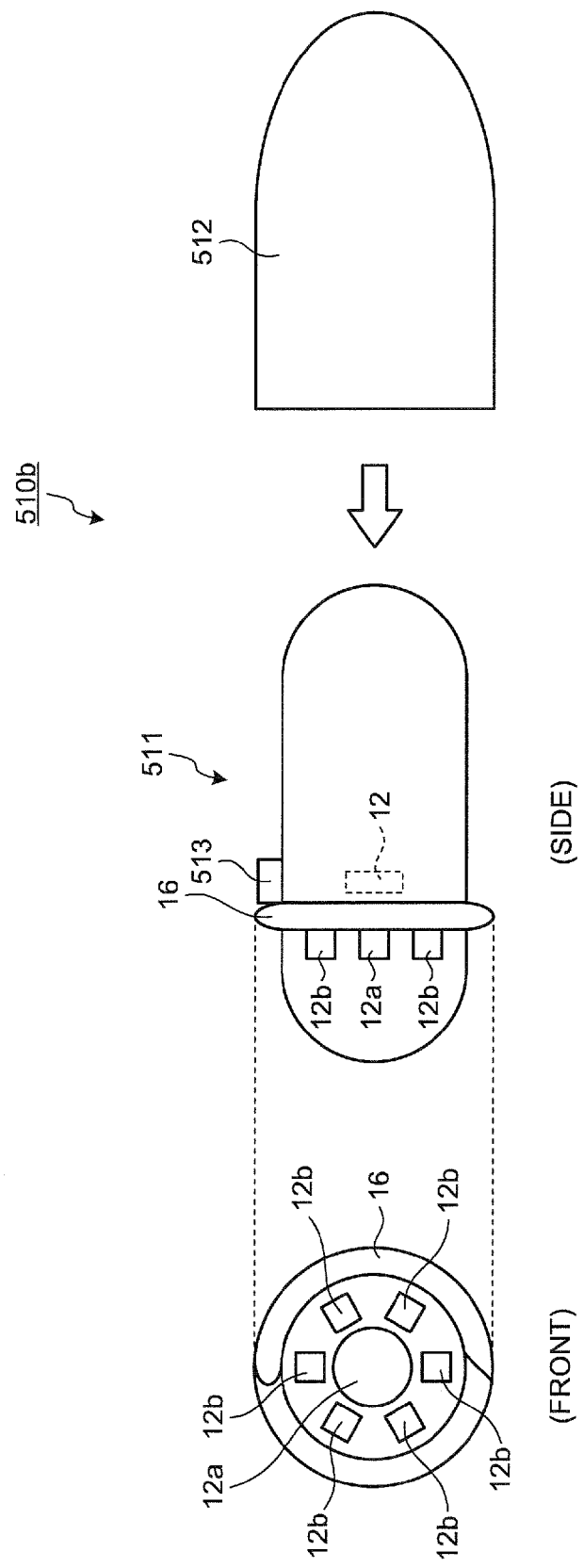
FIG. 46 is a schematic diagram of a configuration example of a capsule endoscope according to a second modification of the present invention.

A second modification of the present invention is explained next. In the fifth embodiment described above, the needle is protruded or retracted by rotational driving of the actuator. In the second modification, the needle is protruded within an image field of an imaging unit. FIG. 46 is a schematic diagram of a configuration example of a capsule endoscope according to the second modification of the present invention. As shown in FIG. 46, a capsule endoscope 510b according to the second modification does not include the helix 521 on an outer surface of a casing and, instead, includes a sheath 512 that covers a capsule main body 511 except for an optical dome. The capsule endoscope 510b further includes a rotational actuator 513 that rotationally drives the needle 16 in the form of approximate semi ring, instead of the motor 520. The capsule main body 511 is a device that includes similar functions to those of the capsule endoscope 510 except for a function of the rotational actuator 513. The remaining parts of the configuration of the second modification are the same as those of the fifth embodiment, and like parts are denoted by like reference letters or numerals.

The needle 16 is an injection needle in the form of helix or approximate semi ring, and is placed near the optical dome of the capsule main body 511 as shown in FIG. 46. The needle 16 is communicated with the valve 14 through a tube or the like and is brought communicated with the medical solution tank 13 by an opening operation for the valve 14. The rotational actuator 513 is rotationally driven by the control circuit on the control board 17 like the motor 520, and rotates the needle 16 to be protruded or retracted. In this case, the rotational actuator 513 causes the needle 16 to protrude within an imaging field of the imaging element 12. The rotational actuator 513 may be placed on the outer surface of the casing of the capsule main body 511 as shown in FIG. 46, or placed within the casing.

The sheath 512 is a part of the casing of the capsule endoscope 510b and is attached to the capsule main body 511 as shown in FIG. 46 to cover the capsule main body 511 except for the optical dome. In this case, the sheath 512 houses the needle 16 before protruding and the rotational actuator 513. The needle 16 within the sheath 512 is protruded from or retracted into the sheath 512 while being rotated by driving force of the rotational actuator 513.

Figure 47:
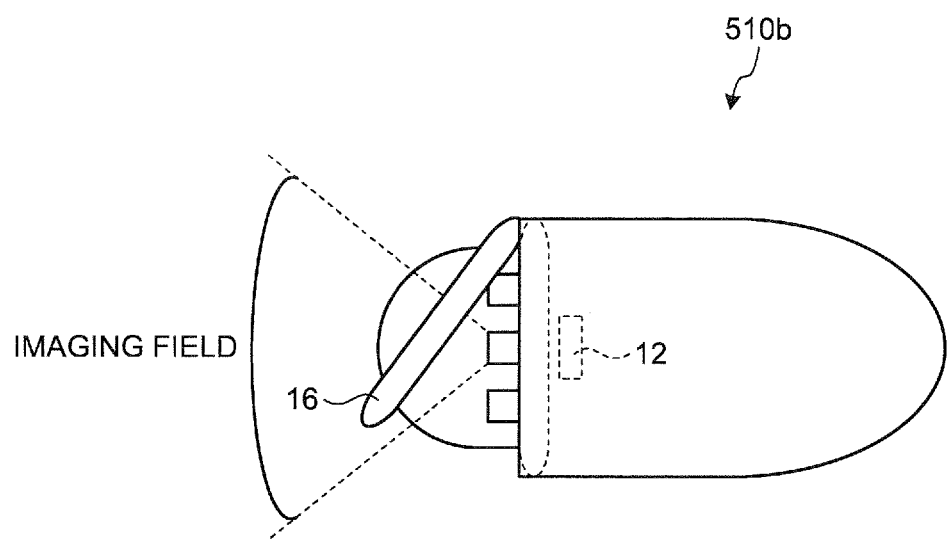
FIG. 47 is a schematic diagram of a state in which the capsule endoscope according to the second modification of the present invention protrudes a needle within an imaging field.
Figure 48:
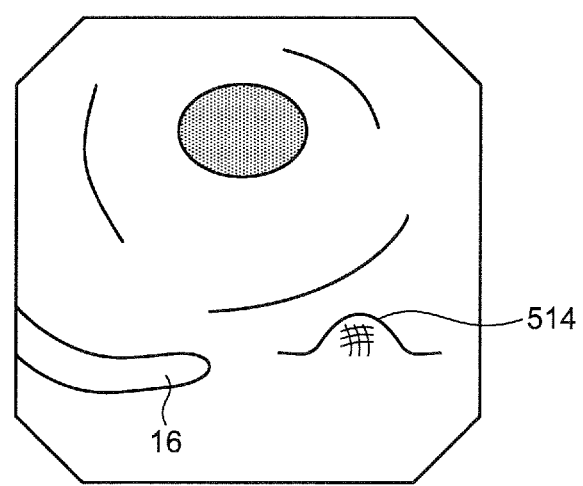
FIG. 48 is a schematic diagram of an example of an image captured by the capsule endoscope according to the second modification of the present invention.

A needle protruding/retracting operation of the capsule endoscope 510b according to the second modification is explained next. FIG. 47 is a schematic diagram of a state in which the capsule endoscope according to the second modification protrudes the needle within the imaging field. FIG. 48 is a schematic diagram of an example of an image captured by the capsule endoscope according to the second modification.

The capsule endoscope 510b inserted into a subject sequentially captures in-vivo images, which are images of insides of organs of the subject while being moved through the insides of the organs of the subject. The capsule endoscope 510b then sequentially wirelessly transmits the captured in-vivo images to the external receiving unit 3 (see FIG. 1). A user such as a doctor or a nurse causes the display unit 5 (see FIG. 1) to display the in-vivo images captured by the capsule endoscope 510b and determines whether the capsule endoscope 510b reaches a desired site such as an affected area within the subject while observing the displayed in-vivo images.

When the capsule endoscope 510b within the subject reaches the desired site in the body, the control unit 4 shown in FIG. 1 generates a control signal based on input information of the input unit 6, and controls the receiving unit 3 to wirelessly transmit the generated control signal to the capsule endoscope 510b. The capsule endoscope 510b captures the in-vivo images while protruding the needle 16 in accordance with the control signal from the control unit 4. In this case, the needle 16 is protruded from the sheath 512 and positioned within the imaging field of the imaging element 12 as shown in FIG. 47. The imaging element 12 captures the in-vivo images including the needle 16 within the imaging field. The in-vivo image captured by the imaging element 12 includes an affected area 514 which is an example of the desired site within the body and the protruded needle 16 as shown in FIG. 48, for example. The user can easily visually confirm a relative position relation between the needle 16 and the affected area 514 by referring to the in-vivo image. The user operates magnetic guidance and needle protruding action of the capsule endoscope 510b while confirming the relative position relation between the needle 16 and the affected area 514 based on the in-vivo image. In accordance with the user operation, the capsule endoscope 510b within the subject can be magnetically guided with the needle 16 protruded near the affected area 514, and accordingly cause the needle 16 to reliably puncture the affected area 514. As a result, the capsule endoscope 510b can reliably inject the medical solution into the affected area 514.

In this way, according to the second modification of the present invention, the injection needle is protruded within the imaging field of the imaging element housed in the capsule endoscope, and the in-vivo images catching relative position relations between a desired site such as an affected area and the injection needle in the subject are captured. Accordingly, the relative position relations between the desired site and the injection needle within the subject can be easily visually confirmed based on the in-vivo images, and the injection needle can be easily stuck in the desired site by operating the magnetic guidance and the needle protruding action of the capsule endoscope while referring to the in-vivo images. As a result, the medical solution can be reliably injected to the desired site without the injection needle being protruded more than necessary after the injection needle punctures an in-vivo site. A condition of injection of the medical solution into the desired site can be visually confirmed by the in-vivo images, and therefore medical solution discharge can be promptly stopped when the medical solution is leaked from the desired site.

The needle protruding action exemplified as the capsule endoscope 510b according to the second modification can be applied to the capsule endoscopes according to the first to fifth embodiments described above. That is, the capsule endoscopes according to the first to fifth embodiments may protrude the injection needle within an imaging field of an imaging element and then capture in-vivo images of the protruded injection needle as an object. Also in these cases, similar operational effects as those of the capsule endoscope 510b according to the second modification described above can be achieved.

Third Modification

A third modification is explained next. In the first to fifth embodiments, the examples in which the needle is protruded by operating the actuator 15 or the motor 520 using the power supplied from the battery 19 are explained. In the third modification, an example in which a needle is protruded using repulsive force between two permanent magnets placed in a casing is explained (Japanese Patent Application No. 2007-46013 filed by the applicant of the present invention, for example). In this case, first and second permanent magnets are provided in a casing of a capsule endoscope such that these permanent magnets can be relatively rotated in a plane including a magnetization direction, and then a magnetic field for relatively rotating any one of the first and second permanent magnets or both thereof in a direction in which the first and second permanent magnets generate repulsive force to each other is applied.

Figure 49:
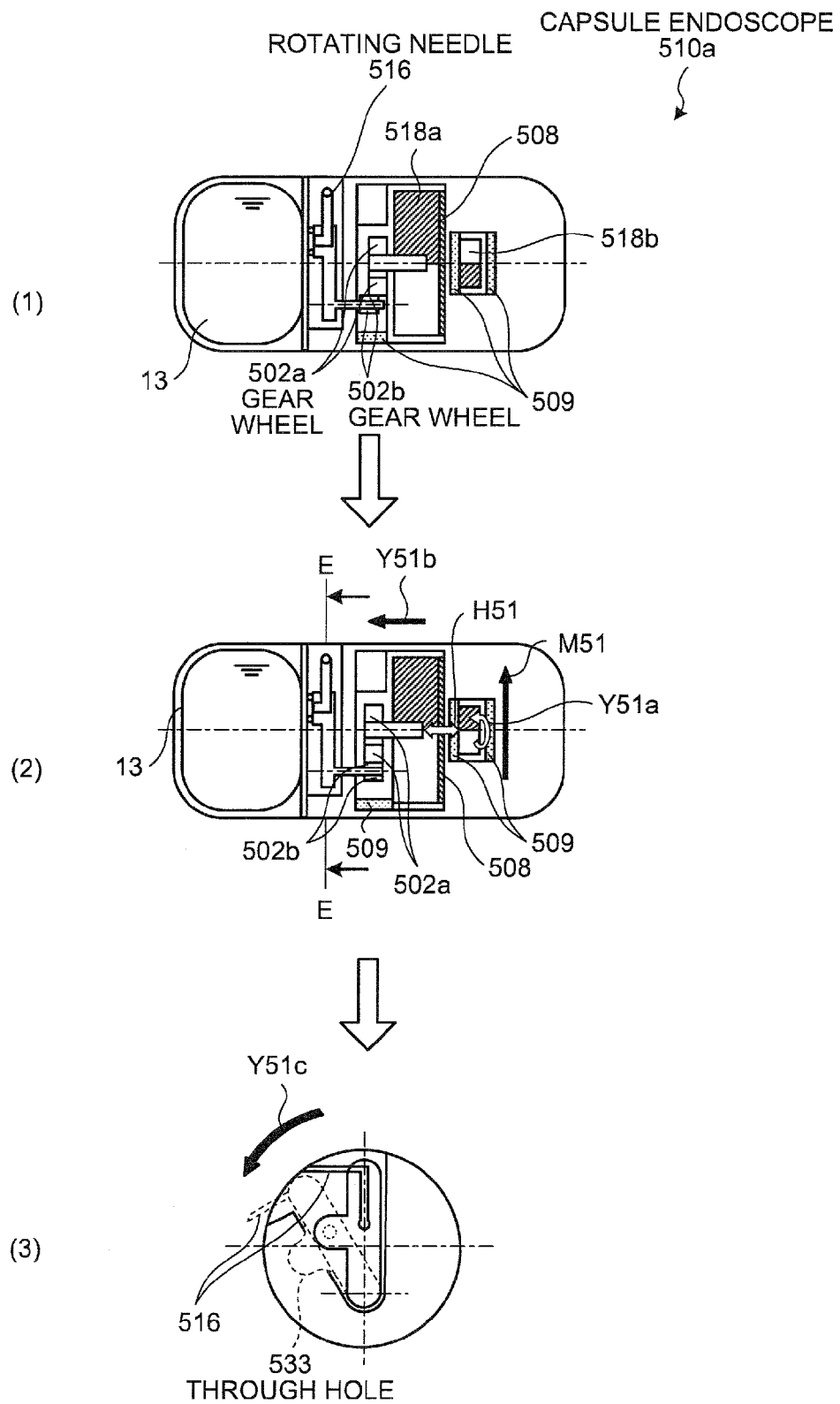
FIG. 49 is a schematic diagram of an internal configuration of a capsule endoscope according to a third modification.
Figure 50:
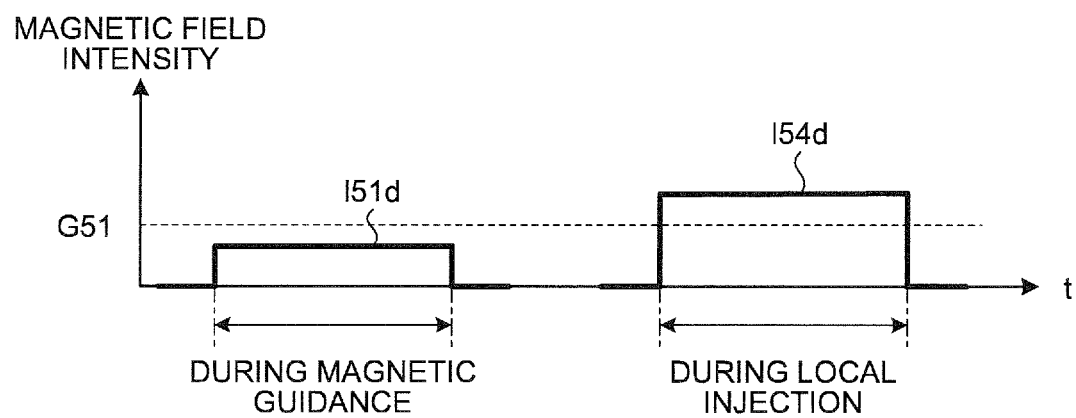
FIG. 50 depicts a magnetic field intensity of a magnetic field applied in predetermined states of the capsule endoscope shown in FIG. 49.

Specifically, the third modification is explained with reference to FIGS. 49 and 50. FIGS. 49(1) and 49(2) are cross-sectional views along an axial direction of a capsule endoscope according to the third modification, and FIG. 49(3) is a cross-sectional view of the capsule endoscope taken along a line E-E in FIG. 49(2). FIG. 50 depicts an intensity of a magnetic field applied by the magnetic field generator 2 in predetermined states of the capsule endoscope according to the third modification. As shown in FIG. 49, in a capsule endoscope 510a according to the third modification, a rotating and moving magnet 518a that is rotatable and movable in a direction shown by an arrow Y51b in FIG. 49(2), and a rotating magnet 518b that is rotatable are provided to face each other. A friction reducing member 509 is provided on a contact surface of the rotating magnet 518b to smoothly rotate the rotating magnet 518b. In the capsule endoscope 510a, a high frictional member 508 is provided on a surface of the rotating and moving magnet 518a on a side of the rotating magnet 518b to restrain rotation when the rotating and moving magnet 518a is brought in contact with a partition on the side of the rotating magnet 518b. The capsule endoscope 510a includes a gear wheel 502b that engages with a gear wheel 502a that is connected to the rotating and moving magnet 518a during rotation of the rotating and moving magnet 518a, thereby controlling a rotational motion of a rotating needle 516.

As shown by a curve 151d in FIG. 50, the magnetic field generator 2 first applies a rotating magnetic field around a long axis of the capsule endoscope 510a with a magnetic field intensity smaller than a magnetic field intensity G51 that enables the rotating and moving magnet 518a having a larger volume than the rotating magnet 518b to rotate. In this case, the rotating and moving magnet 518a is brought into a state where the rotation is restrained by the high frictional member 508, as shown in FIG. 49(1).

During local injection of the medical solution in the medical solution tank 13, the magnetic field generator 2 applies a magnetic field M51 with a magnetic field intensity that is larger than the magnetic field intensity G51 and enables the rotating and moving magnet 518a to rotate in the capsule endoscope 510a, as shown by a curve 154d in FIG. 50. In this case, the rotating and moving magnet 518a and the rotating magnet 518b are rotated in the same direction in accordance with the magnetic field M51, as shown by an arrow Y51a in FIG. 49(2), thereby generating repulsive force H51. As shown by the arrow Y51b in FIG. 49(2), the rotating and moving magnet 518a is moved to the left away from the rotating magnet 518b by the repulsive force H51, so that the gear wheel 502a provided in the rotating and moving magnet 518a engages with the gear wheel 502b. In the rotating and moving magnet 518a, the restrain of the rotation by the high frictional member 508 is cancelled, thereby enabling the magnet 518a to rotate. The capsule endoscope 510a is rotated by application of a magnetic field in a direction corresponding to a rotation direction of the rotating needle 516 with a magnetic field intensity larger than the magnetic field intensity G51, and the gear wheels 502a and 502b are rotated accordingly. As a result, the rotating needle 516 is rotated with rotation of the gear wheel 502b as shown by an arrow Y51c and protrudes outside the capsule endoscope 510a as shown in FIG. 49(3). When the rotating needle 516 is brought in contact with a rotation stop surface, the main body of the capsule endoscope 510a rotates and the rotating needle 516 punctures an intestine wall or the like along a circumferential direction thereof. A through hole 533 of the medical solution tank 13 and a through hole (not shown) of the rotating needle 516 are connected, and accordingly the medical solution in the medical solution tank 13 is injected to a desired area through the rotating needle 516.

When the direction of the magnetic field is reversed with the field intensity larger than the magnetic field intensity G51 being kept, the rotating needle 516 is housed in the capsule endoscope 510a. When the field intensity is made lower than the magnetic field intensity G51 of the applied magnetic field, the rotating and moving magnet 518a is fixed to the capsule endoscope 510a as shown in FIG. 49(1). The needle 16 can be protruded smoothly by using the repulsive force between the two permanent magnets included in the casing.

While the capsule endoscopes that enable optical observation are explained as the body-insertable apparatus systems, the present invention can be applied to a capsule medical apparatus that enables ultrasonic tomographic observations or pH measurements, instead of the optical observations. The present invention can be also applied to a capsule medical apparatus with cord, which is a capsule-shaped casing having an elongated inserting unit attached thereto.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus system comprising a body-insertable apparatus that is inserted into a subject and a control apparatus that controls an operation of the body-insertable apparatus, wherein
the body-insertable apparatus comprises
a magnetic responding unit that is provided within a casing forming the body-insertable apparatus and has a magnetization direction; and
a detecting unit that detects a position and a posture of the body-insertable apparatus;
a needle that is protruded and retracted with respect to a surface of the casing, and
the control apparatus comprises
a magnetic field generator that generates a magnetic field within the subject; and
a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer, and
the control unit is configured to cause the magnetic field generator to generate a first magnetic field for making the body-insertable apparatus have a first posture to be taken immediately before puncture of the needle and to cause the needle to protrude, and configured to generate a second magnetic field for changing an orientation of the entire body-insertable apparatus from the first posture so that the protruded needle punctures the puncture target layer.

2. The body-insertable apparatus system according to claim 1, wherein the control unit changes the orientation of the magnetic responding unit by changing a direction of the magnetic field generated by the magnetic field generator, thereby changing the orientation of the entire body-insertable apparatus.

3. The body-insertable apparatus system according to claim 2, wherein the magnetization direction of the magnetic responding unit is approximately parallel to a radial direction of the casing.

4. The body-insertable apparatus system according to claim 3, wherein the control unit causes the magnetic field generator to generate a rotating magnetic field to rotate the magnetic responding unit, thereby rotating the entire body-insertable apparatus around a long axis of the casing as a center axis.

5. The body-insertable apparatus system according to claim 4, wherein a helical structure that propels the body-insertable apparatus is provided on an outer surface of the casing.

6. A body-insertable apparatus system comprising a body-insertable apparatus that is inserted into a subject and a control apparatus that controls an operation of the body-insertable apparatus, wherein
the body-insertable apparatus comprises
a magnetic responding unit that is provided within a casing forming the body-insertable apparatus and has a magnetization direction; and
a needle that is protruded and retracted with respect to a surface of the casing, and the control apparatus comprises
a magnetic field generator that generates a magnetic field within the subject; and
a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer;
wherein the control unit changes the orientation of the magnetic responding unit by changing a direction of the magnetic field generated by the magnetic field generator, thereby changing the orientation of the entire body-insertable apparatus;
the magnetization direction of the magnetic responding unit is approximately parallel to a radial direction of the casing; and
the control unit causes the magnetic field generator to generate a rotating magnetic field to rotate the magnetic responding unit, thereby rotating the entire body-insertable apparatus around a long axis of the casing as a center axis; and
further comprising a connecting member that connects the magnetic responding unit to the casing and switches a connection state of the magnetic responding unit with respect to the casing between a fixed state and a movable state.

7. The body-insertable apparatus system according to claim 6, wherein the movable state of the magnetic responding unit is a state where the magnetic responding unit is movable relative to the casing.

8. The body-insertable apparatus system according to claim 7, further comprising a protruding and retracting mechanism that protrudes or retracts the needle from or into the casing in accordance with relative rotation of the magnetic responding unit with respect to the casing.

9. The body-insertable apparatus system according to claim 7, wherein the body-insertable apparatus rotates with rotation of the magnetic responding unit in the fixed state with respect to the casing.

10. A body-insertable apparatus system comprising a body-insertable apparatus that is inserted into a subject and a control apparatus that controls an operation of the body-insertable apparatus, wherein
the body-insertable apparatus comprises
a magnetic responding unit that is provided within a casing forming the body-insertable apparatus and has a magnetization direction; and
a needle that is protruded and retracted with respect to a surface of the casing, and
the control apparatus comprises
a magnetic field generator that generates a magnetic field within the subject; and
a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer;
wherein the control unit changes the orientation of the magnetic responding unit by changing a direction of the magnetic field generated by the magnetic field generator, thereby changing the orientation of the entire body-insertable apparatus; and
the needle is positioned such that the distal end direction of the needle is in a same plane as the magnetization direction of the magnetic responding unit.

11. The body-insertable apparatus system according to claim 10, wherein the needle has a length that realizes a distance between a distal end of the protruded needle and an outer circumference of the casing equal to or larger than 1 millimeter on a line connecting the distal end of the protruded needle and a long axis of the casing by a most direct way.

12. The body-insertable apparatus system according to claim 11, wherein an angle of the needle formed by an external tangent of the needle on a side of the casing and a tangent line at a position where the generatrix intersects with the outer circumference of the casing is equal to or smaller than 45°.

13. The body-insertable apparatus system according to claim 11, wherein a length of the needle when protruded is equal to or larger than 1.26 millimeters.

14. The body-insertable apparatus system according to claim 11, wherein an outside diameter of the casing is equal to or smaller than 20 millimeters.

15. The body-insertable apparatus system according to claim 11, wherein a length (L) of the needle when protruded has a relation with an outside diameter (2r) of the casing:

$$L+2^{1/2}(r/2) \geq (r^2/2+2r+1)^{1/2}.$$

16. A body-insertable apparatus system comprising a body-insertable apparatus that is inserted into a subject and a control apparatus that controls an operation of the body-insertable apparatus, wherein
the body-insertable apparatus comprises
a magnetic responding unit that is provided within a casing forming the body-insertable apparatus and has a magnetization direction; and
a needle that is protruded and retracted with respect to a surface of the casing, and
the control apparatus comprises
a magnetic field generator that generates a magnetic field within the subject; and
a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer;
wherein the control unit changes the orientation of the magnetic responding unit by changing an intensity of the magnetic field generated by the magnetic field generator, thereby changing the orientation of the entire body-insertable apparatus; and
the magnetization direction of the magnetic responding unit is approximately parallel to a long axis direction of the casing.

17. A body-insertable apparatus system comprising a body-insertable apparatus that is inserted into a subject and a control apparatus that controls an operation of the body-insertable apparatus, wherein
the body-insertable apparatus comprises
a magnetic responding unit that is provided within a casing forming the body-insertable apparatus and has a magnetization direction; and a needle that is protruded and retracted with respect to a surface of the casing, and the control apparatus comprises a magnetic field generator that generates a magnetic field within the subject; and a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer;

wherein the needle has a distal end cut at an angle about 30°.

18. The body-insertable apparatus system according to claim 17, wherein the needle is positioned in the casing to cause a cut surface to face an outer side of the casing.

19. A body-insertable apparatus system comprising a body-insertable apparatus that is inserted into a subject and a control apparatus that controls an operation of the body-insertable apparatus, wherein the body-insertable apparatus comprises a magnetic responding unit that is provided within a casing forming the body-insertable apparatus and has a magnetization direction; and a needle that is protruded and retracted with respect to a surface of the casing, and the control apparatus comprises a magnetic field generator that generates a magnetic field within the subject; and a control unit that causes the magnetic field generator to generate a magnetic field for changing an orientation of the magnetic responding unit based on the magnetization direction of the magnetic responding unit in the body-insertable apparatus, a position of the needle in the body-insertable apparatus, and a distal end direction of the needle, thereby changing an orientation of the entire body-insertable apparatus to enable the protruded needle to puncture a puncture target layer;

wherein the body-insertable apparatus includes an image obtaining unit that obtains in-vivo images of the subject, and the needle is positioned within a visual field of the image obtaining unit when protruded outside the casing.

* * * * *